United States Patent
Sham

(10) Patent No.: US 11,826,162 B2
(45) Date of Patent: Nov. 28, 2023

(54) METHODS AND SYSTEMS FOR VAGINAL THERAPEUTIC DEVICE FITTING

(71) Applicant: COSM MEDICAL CORP., Toronto (CA)

(72) Inventor: Derek Sham, Toronto (CA)

(73) Assignee: COSM Medical Corp., Toronto (CA)

( * ) Notice: Subject to any disclaimer, the term of this patent is extended or adjusted under 35 U.S.C. 154(b) by 580 days.

(21) Appl. No.: 16/648,582

(22) PCT Filed: Sep. 18, 2018

(86) PCT No.: PCT/CA2018/000173
§ 371 (c)(1),
(2) Date: Mar. 18, 2020

(87) PCT Pub. No.: WO2019/051579
PCT Pub. Date: Mar. 21, 2019

(65) Prior Publication Data
US 2020/0214617 A1    Jul. 9, 2020

Related U.S. Application Data

(60) Provisional application No. 62/559,853, filed on Sep. 18, 2017.

(51) Int. Cl.
*A61B 5/00* (2006.01)
*A61B 5/107* (2006.01)
(Continued)

(52) U.S. Cl.
CPC .......... *A61B 5/4337* (2013.01); *A61B 5/0024* (2013.01); *A61B 5/01* (2013.01);
(Continued)

(58) Field of Classification Search
CPC ... G16H 50/50; A61F 2013/8491; A61F 6/08; A61F 5/107; A61F 5/1076; A61F 5/202;
(Continued)

(56) References Cited

U.S. PATENT DOCUMENTS

| 4,681,572 A | 7/1987 | Tokarz et al. |
|---|---|---|
| 7,717,892 B2 | 5/2010 | Bartning et al. |

(Continued)

FOREIGN PATENT DOCUMENTS

| CN | 106915072 A | 7/2017 |
|---|---|---|
| EP | 1096901 A1 | 5/2001 |

(Continued)

OTHER PUBLICATIONS

PCT International Search Report and Written Opinion for PCT Application No. PCT/CA2018/000173 dated Jan. 11, 2019 (11 pages).

(Continued)

*Primary Examiner* — Christine H Matthews
(74) *Attorney, Agent, or Firm* — Stratford Group Ltd.

(57) ABSTRACT

A variety of medical and non-medical devices are exploited by users to address a wide range of conditions. However, in the vast majority of instances, the device has a limited number of options with respect to its fit for the user and its performance. Further, the determination of target performance and fit are established on a qualitative basis rather than a quantitative basis. In many instances, these combinations lead to low user acceptance of the device due to the resulting performance and fit issues. Accordingly, it would enhance performance and user acceptance if a quantitative determination provided a recommended type where options exist, and this determination provided the basis of a custom designed device to the user's specific anatomical and/or performance requirements.

16 Claims, 20 Drawing Sheets

(51) Int. Cl.

| | |
|---|---|
| *A61F 6/08* | (2006.01) |
| *B33Y 80/00* | (2015.01) |
| *G16H 20/40* | (2018.01) |
| *G16H 50/20* | (2018.01) |
| *G16H 30/40* | (2018.01) |
| *A61B 5/01* | (2006.01) |
| *A61B 5/22* | (2006.01) |
| *A61B 8/12* | (2006.01) |
| *A61B 5/391* | (2021.01) |
| *A61B 5/20* | (2006.01) |
| *A61B 8/08* | (2006.01) |

(52) U.S. Cl.
CPC ............ *A61B 5/1076* (2013.01); *A61B 5/227* (2013.01); *A61B 5/391* (2021.01); *A61B 8/12* (2013.01); *A61F 6/08* (2013.01); *G16H 20/40* (2018.01); *G16H 30/40* (2018.01); *G16H 50/20* (2018.01); A61B 5/205 (2013.01); A61B 8/0858 (2013.01); A61B 2560/0406 (2013.01); A61B 2562/12 (2013.01); *B33Y 80/00* (2014.12)

(58) Field of Classification Search
CPC .......... A61F 5/205; A61F 5/224; A61F 5/227; A61F 5/4337
See application file for complete search history.

(56) References Cited

U.S. PATENT DOCUMENTS

| | | | |
|---|---|---|---|
| 10,687,977 B1* | 6/2020 | Hardart | ................. A61F 6/08 |
| 2007/0167819 A1* | 7/2007 | Osborn, III | ........... A61B 8/485 |
| | | | 600/462 |
| 2009/0266367 A1 | 10/2009 | Ziv et al. | |
| 2010/0076255 A1 | 3/2010 | Robertson et al. | |
| 2015/0196802 A1 | 7/2015 | Siegel | |

FOREIGN PATENT DOCUMENTS

| | | |
|---|---|---|
| EP | 2229884 A1 | 9/2010 |
| GB | 2426589 B | 11/2010 |
| WO | 2015108655 A1 | 7/2015 |

OTHER PUBLICATIONS

First Office Action received for Chinese Application No. 201880068011.X, dated Aug. 2, 2021. (English Translation Provided).
Decision to Grant received for Chinese Application No. 201880068011.X, dated Feb. 22, 2022. (English Translation Provided).

* cited by examiner

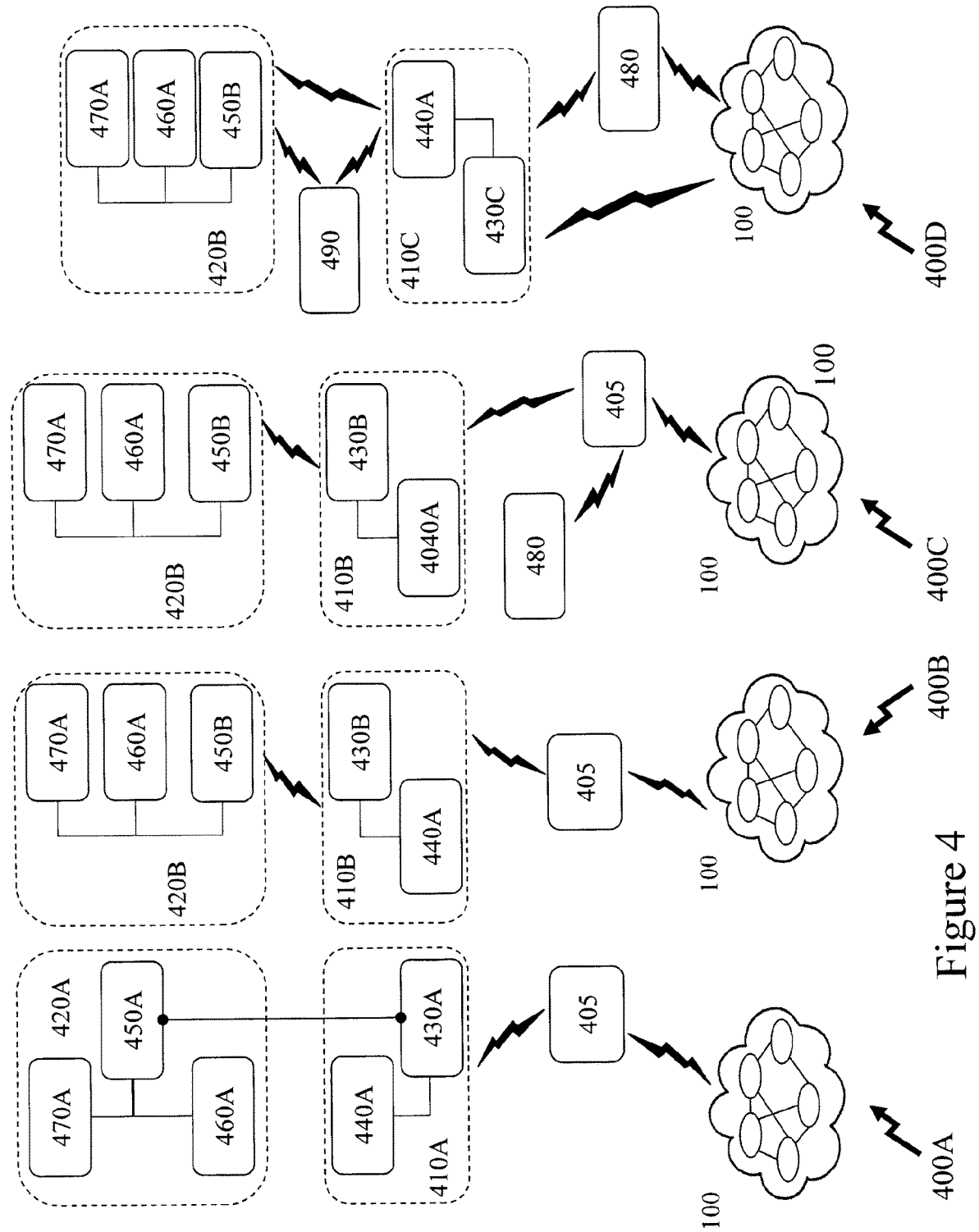

METHODS AND SYSTEMS FOR VAGINAL THERAPEUTIC DEVICE FITTING

BACKGROUND

The present invention relates to vaginal therapeutic devices and more methods and systems for establishing a custom fitting or an enhanced fitting of such vaginal therapeutic devices.

For women within these medical conditions pelvic organ prolapse (POP) and urinary incontinence (UI) are common and often distressing conditions. Research indicates that in the United States alone there are 3.3 million women with pelvic organ prolapse and approximately 300,000 surgeries are performed annually in the United States. Additionally, between approximately 25% of all women, 33% of older women, have some degree of urinary incontinence. Further, male urinary incontinence whilst it exists has only recently become perhaps evident to the general population with the advent of advertisements for male and female incontinence underwear. An aging population at this point would not indicate any reduction in such figures in the near term whilst a massive expenditure and ease of availability of ultra-thin liners for women's underwear, male and female incontinence underwear and emerging products such as liners for male underwear within supermarkets and pharmacies indicate that the demand and market are high enough for multinational household product and pharmaceutical enterprises to have product lines and brands in this area.

As a result, POP studies frequently have prominent numbers of women over the age of 50 and Caucasian, rather than including young women who have given birth and a more diverse balance of women from multiple races and nationalities. Accurate data related to occurrence and impact of POP will be more readily attainable after POP becomes common knowledge and as studies related to POP are now beginning to become more widespread. Today, it is not uncommon for women to not disclose indicators of POP to physicians because of embarrassment related to the symptoms.

POP encompasses the widest demographic of all women's health issues and the dynamics behind POP are likely to be more diverse than any other health condition women will experience. Multiple types of POP display a variety of symptoms; women's unique childbirth, occupation, genetics, general health, and social activities history vary significantly, and the demographic variables are diverse.

There are a range of surgical treatment options for POP as well as non-surgical treatments. Non-surgical treatment options include Kegel exercises, Kegel assist devices, pessaries, core/floor strengthening exercises, biofeedback, electrical stimulation, hormone replacement therapy, tibial nerve stimulation and support garments. However, despite the wide demographic, the multiple types of POP, and the uniqueness of every woman the non-surgical solutions available such as Kegel assist devices and pessaries etc. are fitted today by best guess, trial-and-error, or incorrectly. The Internet is replete with articles either explaining to medical personnel how to fit a pessary or explaining to users how to tell if their pessary fits correctly.

Whilst manufacturers understand the need for a range of sizes the result is a plethora of types and sizes for the medical personnel to select from and employ. For example, the "Folding Smith" pessary design is available in 10 standard sizes as outlined below in Table 1. Repeat such a number of options for each different pessary design and the result is a logistical nightmare for a medical facility offering fitting of pessaries, a bewildering number of options with different characteristics per design, and either lots of trial-and-error to achieve a successful outcome or more likely a series of fittings and a patient stopping from frustration. Even amongst the medical profession, most clinicians tend to view the pessary with a mixture of reluctance and disregard.

Against this study data indicates that approximately 90% of patients can be successfully treated with a non-pharmaceutical and/or non-surgical solution that has very few contraindications.

TABLE 1

Exemplary Size Options for Folding Smith Pessary

| Size | Length (inch) | Width (inch) |
|---|---|---|
| 0 | 3⅛ | 2 |
| 1 | 3¼ | 2⅛ |
| 2 | 3½ | 2¼ |
| 3 | 3¾ | 2⅜ |
| 4 | 4¼ | 2½ |
| 5 | 4½ | 2⅝ |
| 6 | 4¾ | 2¾ |
| 7 | 5 | 2⅞ |
| 8 | 5½ | 3 |
| 9 | 5¾ | 3⅛ |

Accordingly, it would be beneficial to provide medical personnel with a quantitative rather than a qualitative basis for the determination of the size of a pessary vaginal therapeutic device (VTD), or other VTD. It would be further beneficial for the quantitative based determination to provide a recommended type where multiple types are options. It would be further beneficial for the quantitative based determination to provide the basis of a custom designed pessary VTD or other VTD to the user's specific anatomical requirements and/or POP/UI characteristics. It would also be evident that a variety of user specific therapeutic devices (USTDs) such as orthotics and orthopedics exhibit similar issues in respect of them benefiting from the application of a design and simulation process exploiting user specific and application specific data.

Other aspects and features of the present invention will become apparent to those ordinarily skilled in the art upon review of the following description of specific embodiments of the invention in conjunction with the accompanying figures.

SUMMARY

It is an object of the present invention to mitigate limitations within the prior art relating to vaginal therapeutic devices and more methods and systems for establishing a custom fitting or an enhanced fitting of such vaginal therapeutic devices.

In accordance with an embodiment of the invention there is provided a method of providing a vaginal therapeutic device (VTD) for a user comprising:
deriving one or more user specific results by performing a measurement and characterization process upon the user comprising at least one measurement of a plurality of measurements;
performing an assessment and modelling process for transferring the one or more user specific results of the measurement and characterization process to an anatomical model;

defining the VTD comprising at least one structure of a plurality of structures, each structure of defined geometry and material composition; and fabricating the plurality of structures of defined geometry and material composition by a plurality of process steps, each process step being either an additive manufacturing step or a non-additive manufacturing step.

In accordance with an embodiment of the invention there is provided a device for assessing characteristics of a user comprising:

a first predetermined portion for insertion into a vagina of a user;

a second predetermined portion electrically coupled to the first predetermined portion;

at least one sensor of a plurality of sensors wherein the sensor is selected from the group comprising a photoplethysmography sensor, a laser Doppler imaging sensor, a phonomyography sensor, a pressure sensor, a force sensor, a pH sensor, and a temperature sensor.

In accordance with an embodiment of the invention there is provided a device for assessing characteristics of a user comprising:

a body formed from a highly elastic and deformable material;

a plurality of sensors disposed upon the surface of the body, each sensor to measure local deformation of the body; and a plurality of contacts electrically connected to each sensor allowing local deformation measurements to be taken.

In accordance with an embodiment of the invention there is provided a method of generating a customized prosthetic device for a user comprising:

establishing an anatomical model relating to a vagina and its surrounding support tissues and pelvic organs;

modifying the anatomical model in dependence upon one or more user specific results obtained by performing a measurement and characterization process upon the user comprising at least one measurement of a plurality of measurements; and defining the VTD comprising a plurality of structures of defined geometry and material composition in dependence upon the modified anatomical model.

In accordance with an embodiment of the invention there is provided a device comprising:

a first portion comprising:
 a body portion formed from a first predetermined material having a first Young's modulus defining a recess on a first side and a ring, the ring formed around an opening on said first side;
 a stub portion formed on a second side of the first portion distal to the first side formed from a second predetermined material having a second Young's modulus extending away from the first portion and having a first predetermined arcuate profile;

a second portion comprising:
 a knob portion attached to the distal end of the stub portion from the body portion formed from a third predetermined material having a third Young's modulus;
and
a third portion formed from a fourth predetermined material having a fourth Young's modulus having a first section disposed within the body portion and a second section disposed within the stub portion; wherein
a predetermined portion of the first section and a second predetermined portion of the second section form part of a second predetermined arcuate profile.

In accordance with an embodiment of the invention there is provided a device comprising:

a body portion formed from a first predetermined material having a first Young's modulus and having a first predetermined geometry;

a second portion formed from a second predetermined material having a second Young's modulus having one or more sections disposed within the body portion, each section having a second predetermined geometry; wherein the first predetermined geometry, the second predetermined geometry, the first predetermined material, and second predetermined material are established in dependence upon a physical characterization of a user for whom the device is intended and a modelling and simulation process which employs the physical characterization data;

the device is a predominantly ring like pessary, a predominantly disk like pessary, and a space filling pessary.

In accordance with an embodiment of the invention there is provided a device comprising:

a body portion formed from a first predetermined material having a first Young's modulus defining a frustum comprising a predetermined section of a conical body having a predetermined outer profile with a predetermined portion removed such that the inner surface of the body portion has a predetermined inner profile and there are openings at either end of the body portion;

a knob portion formed from a second predetermined material having a second Young's modulus disposed at a predetermined position on the external surface of the body portion; and a first resilient element of a plurality of resilient elements disposed within the body portion, each resilient element formed from a third predetermined material having a third Young's modulus and disposed at a predetermined position within the body portion.

In accordance with an embodiment of the invention there is provided a method of providing a user specific therapeutic device (USTD) for a user comprising:

deriving one or more user specific results by performing a measurement and characterization process upon the user comprising at least one measurement of a plurality of measurements;

performing an assessment and modelling process for transferring the one or more user specific results of the measurement and characterization process to an anatomical model;

defining the USTD comprising at least one structure of a plurality of structures, each structure of defined geometry and material composition; and fabricating the plurality of structures of defined geometry and material composition by a plurality of process steps, each process step being either an additive manufacturing step or a non-additive manufacturing step.

In accordance with an embodiment of the invention there is provided a device comprising:

an inflatable balloon;

a coupling for demountably attaching a fluidic system to the inflatable balloon; and a ring disposed at one end of the inflatable balloon; wherein the ring has a first predetermined geometry and is formed from a predetermined material.

In accordance with an embodiment of the invention there is provided a method comprising:

disposing a balloon within a vagina of a user;

coupling the balloon to a device which comprises at least one ultrasonic transducer of a plurality of ultrasonic transducers disposed with respect to the fitting to couple ultrasonic signals to and from the fluid within the balloon;

filling the balloon with a predetermined fluid to a predetermined threshold;

generating ultrasonic signals with the at least one ultrasonic transducer of the plurality of ultrasonic transducers;

receiving reflected ultrasonic signals with another ultrasonic transducer of the plurality of ultrasonic transducers; and processing the reflected ultrasonic signals with a processing circuit within the device.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 4 depicts different USTD and electronic device configurations as may be supported by embodiments of the invention;

DETAILED DESCRIPTION

Figure 1:
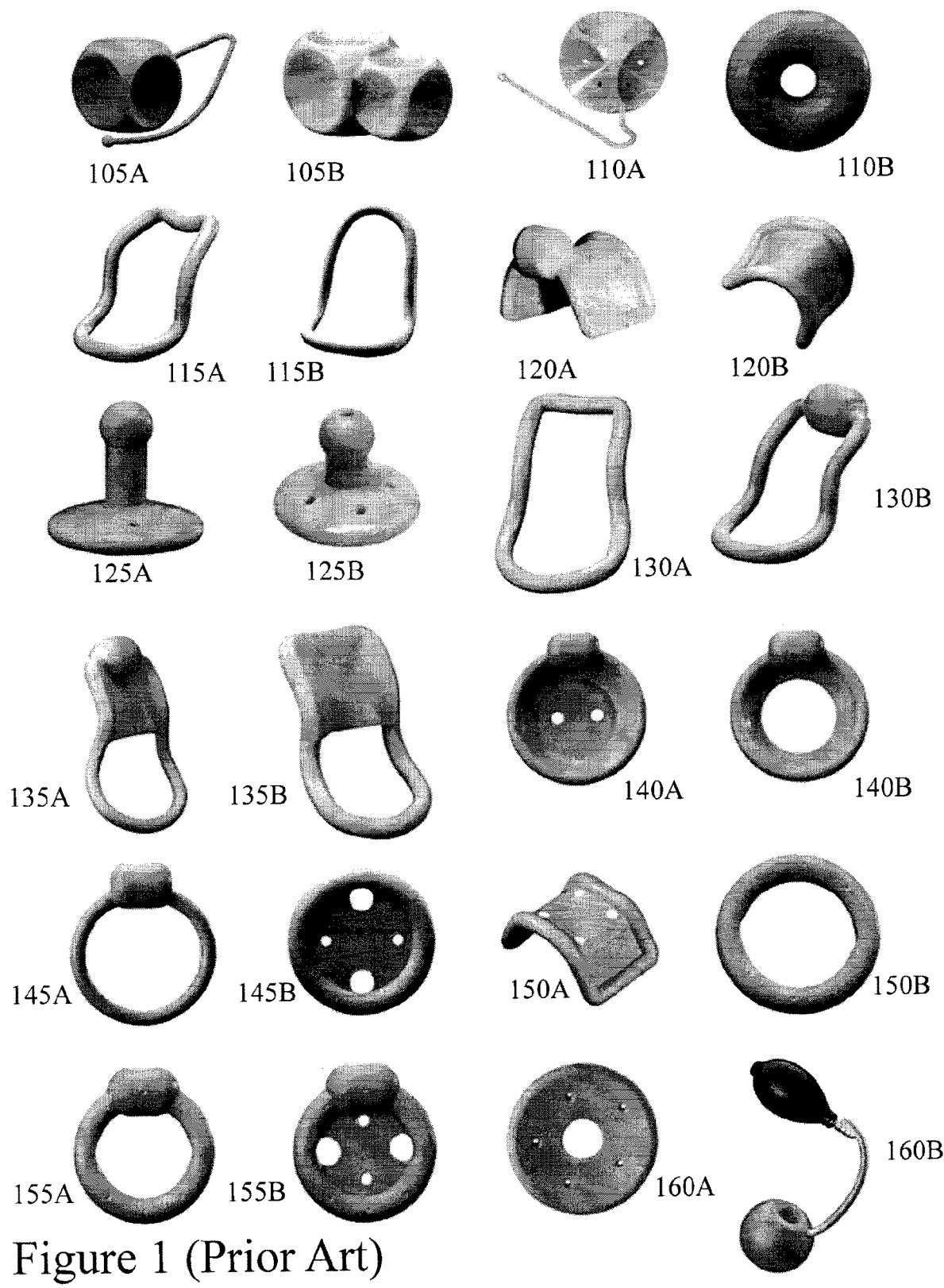
FIG. 1 depicts common types of pessary type user specific therapeutic device (USTD) according to the prior art.

The present invention is directed to vaginal therapeutic devices and more methods and systems for establishing a custom fitting or an enhanced fitting of such vaginal therapeutic devices.

The ensuing description provides representative embodiment(s) only, and is not intended to limit the scope, applicability or configuration of the disclosure. Rather, the ensuing description of the embodiment(s) will provide those skilled in the art with an enabling description for implementing an embodiment or embodiments of the invention. It being understood that various changes can be made in the function and arrangement of elements without departing from the spirit and scope as set forth in the appended claims. Accordingly, an embodiment is an example or implementation of the inventions and not the sole implementation. Various appearances of "one embodiment," "an embodiment" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention can also be implemented in a single embodiment or any combination of embodiments.

Reference in the specification to "one embodiment", "an embodiment", "some embodiments" or "other embodiments" means that a particular feature, structure, or characteristic described in connection with the embodiments is included in at least one embodiment, but not necessarily all embodiments, of the inventions. The phraseology and terminology employed herein is not to be construed as limiting but is for descriptive purpose only. It is to be understood that where the claims or specification refer to "a" or "an" element, such reference is not to be construed as there being only one of that element. It is to be understood that where the specification states that a component feature, structure, or characteristic "may", "might", "can" or "could" be included, that particular component, feature, structure, or characteristic is not required to be included.

Reference to terms such as "left", "right", "top", "bottom", "front" and "back" are intended for use in respect to the orientation of the particular feature, structure, or element within the figures depicting embodiments of the invention. It would be evident that such directional terminology with respect to the actual use of a device has no specific meaning as the device can be employed in a multiplicity of orientations by the user or users. Reference to terms "including", "comprising", "consisting" and grammatical variants thereof do not preclude the addition of one or more components, features, steps, integers or groups thereof and that the terms are not to be construed as specifying components, features, steps or integers. Likewise, the phrase "consisting essentially of", and grammatical variants thereof, when used herein is not to be construed as excluding additional components, steps, features integers or groups thereof but rather that the additional features, integers, steps, components or groups thereof do not materially alter the basic and novel characteristics of the claimed composition, device or method. If the specification or claims refer to "an additional" element, that does not preclude there being more than one of the additional element.

"Artificial intelligence" (AI, also machine intelligence, MI) as used herein may refer to, but is not limited to, intelligence exhibited by machines rather than humans or other animals which exhibit so-called natural intelligence (NI). Colloquially, the term AI is employed when a machine mimics "cognitive" functions which humans associate with other human minds, such as "learning" and "problem solving". AI may employ one or more tools, including, but not limited to search and optimization, logic, probabilistic methods for uncertain reasoning, classifiers and statistical learning methods, neural networks, deep feedforward neural networks, deep recurrent neural networks, and control theory.

A "portable electronic device" (PED) as used herein and throughout this disclosure, refers to a wireless device used for communications and other applications that requires a battery or other independent form of energy for power. This includes devices, but is not limited to, such as a cellular telephone, smartphone, personal digital assistant (PDA), portable computer, pager, portable multimedia player, portable gaming console, laptop computer, tablet computer, a wearable device, an electronic reader, a vaginal therapy device (VTD), and a user specific therapeutic device (USTD).

A "fixed electronic device" (FED) as used herein and throughout this disclosure, refers to a wireless and/or wired device used for communications and other applications that requires connection to a fixed interface to obtain power. This includes, but is not limited to, a laptop computer, a personal computer, a computer server, a kiosk, a gaming console, a digital set-top box, an analog set-top box, an Internet enabled appliance, an Internet enabled television, and a multimedia player.

An "application" (commonly referred to as an "app") as used herein may refer to, but is not limited to, a "software application", an element of a "software suite", a computer program designed to allow an individual to perform an activity, a computer program designed to allow an electronic device to perform an activity, and a computer program designed to communicate with local and/or remote electronic devices. An application thus differs from an operating system (which runs a computer), a utility (which performs maintenance or general-purpose chores), and a programming tools (with which computer programs are created). Generally, within the following description with respect to embodiments of the invention an application is generally presented in respect of software permanently and/or temporarily installed upon a PED and/or FED.

A "user" as used herein may refer to, but is not limited to, an individual exploiting a vaginal therapeutic device according to an embodiment or embodiments of the invention. As such an individual may be employing a vaginal therapeutic device with respect to one or more conditions, requirements, and/or preventions. As such an individual may include, but not be limited to, a female human, a female animal, a recipient of sex reassignment surgery, a recipient of gender confirmation surgery, gender specific reconstruction surgery, gender affirming surgery, and sex realignment surgery. In its broadest sense the user may further include, but not be limited to, mechanical systems, robotic systems, android systems, etc. that may be characterised by a requirement to exploit one or more embodiments of the invention. A user may be associated with biometric data which may be, but not limited to, monitored, acquired, stored, transmitted, processed and analysed either locally or remotely to the user. A user may also be associated through one or more accounts and/or profiles with one or more of a service provider, third party provider, enterprise, social network, social media etc. via a dashboard, web service, website, software plug-in, software application, and graphical user interface.

The terms "woman" or "female" as used herein, and throughout this disclosure, refers to a human having a vagina or surgically formed vaginal structure and optionally a clitoris or clitoral region, uterus, a urethra, and/or an anus. The terms "woman" and "female" are used interchangeably herein.

"User information" as used herein may refer to, but is not limited to, user behavior information and/or user profile information. It may also include a user's biometric information, an estimation of the user's biometric information, or a projection/prediction of a user's biometric information derived from current and/or historical biometric information.

A "vaginal therapeutic device" (VTD, commonly referred to as a pessary) refers to a medical device and is a specific form of a user specific therapeutic device (USTD). A VTD may be used to support the uterus, vagina, bladder, or rectum. A VTD may be employed to treat a pelvic organ prolapse (POP), such as prolapse of the uterus for example, treat an intestinal issue, an enterocele (essentially a vaginal hernia), reduce the impact of an evolving POP, treat and/or reduce the impact of urinary incontinence (UI), treat and/or reduce the impact of stress UI, and treat and/or reduce the impact of urge UI. Alternatively, a VTD may be employed during pregnancy to treat an incompetent (or insufficient) cervix (cervix starts to shorten and open too early) as an alternative to cervical cerclage since there are fewer potential complications. A VTD may also be used to address a fecal incontinence, retroverted uterus, address cystocele, address rectocele, induce an abortion, or provide and/or support contraception. A VTD may be placed temporarily or permanently. A pharmaceutical VTD may provide an effective means for the delivery of one or more pharmaceutical substances which are easily absorbed through the skin of the vagina, or intended to have action in the locality, for example against inflammation or infection, or on the uterus. An occlusive VTD may perform similarly to a cervical cap and may be used in combination with spermicide as a contraception. A stem VTD, a type of occlusive VTD, is an early form of the cervical cap shaped like a dome to cover the cervix but with a central rod or "stem" entering the uterus to hold it in place. VTD's within the prior art are offered in a variety of forms including, but not limited, ring VTDs, lever VTDs, Gehrung VTDs, inflatable VTDs, doughnut VTDs, cube VTDs, Gellhorn VTDs, and incontinence VTDs. VTDs according to embodiments of the invention are designed in dependence upon the user for custom fitting and/or applications including, but not limited to, prolapse, urinal incontinence, and fecal incontinence.

"Sex reassignment surgery" (SRS, also known as gender reassignment surgery, gender confirmation surgery, genital reconstruction surgery, gender-affirming surgery, or sex realignment surgery) as used herein may refer to, but is not limited to, one or more surgical procedures that adjust a user's physical appearance and function with respect to their genitalia which may require the user to use a vaginal therapeutic device according to an embodiment of the invention.

A "wearable device" or "wearable sensor" relates to miniature electronic devices that are worn by the user including those under, within, with or on top of clothing and are part of a broader general class of wearable technology which includes "wearable computers" which in contrast are directed to general or special purpose information technologies and media development. Such wearable devices and/or wearable sensors may include, but not be limited to, smartphones, smart watches, e-textiles, smart shirts, activity trackers, smart glasses, environmental sensors, medical sensors, biological sensors, physiological sensors, chemical sensors, ambient environment sensors, position sensors, neurological sensors, drug delivery systems, medical testing and diagnosis devices, and motion sensors. The wearable devices and/or wearable sensors may include, but not be limited to, devices that can stimulate and/or measure parameters that are designed to fit within, on, or near the vagina, urethra, uterus, bladder, cervix, colon, anal sphincter, urethral sphincter, and abdominal cavity as well as intraabdominal pressure can be correlated to the amount of force that the VTD will need to support.

"Biometric" information as used herein may refer to, but is not limited to, data relating to a user characterised by data relating to a subset of conditions including, but not limited to, their environment, medical condition, biological condition, physiological condition, chemical condition, ambient environment condition, position condition, neurological condition, drug condition, and one or more specific aspects of one or more of these said conditions. Accordingly, such biometric information may include, but not be limited, blood oxygenation, blood pressure, blood flow rate, heart rate, temperate, fluidic pH, viscosity, particulate content, solids content, altitude, vibration, motion, perspiration, EEG, ECG, energy level, etc. In addition, biometric information may include data relating to physiological characteristics related to the shape and/or condition of the body wherein examples may include, but are not limited to, fingerprint, facial geometry, baldness, DNA, hand geometry, odour, and scent. Biometric information may also include data relating to behavioral characteristics, including but not limited to, typing rhythm, gait, and voice.

A "profile" as used herein, and throughout this disclosure, refers to a computer and/or microprocessor readable data file comprising data relating to a VTD according to an embodiment of the invention and/or biometric data of a user.

A "scaffold" or "scaffolds" as used herein, and throughout this disclosure, refers to a structure that is used to hold up, interface with, or support another material or element(s). This includes, but is not limited to, such two-dimensional (2D) structures such as substrates and films, three-dimensional (3D) structures such as geometrical objects, non-geometrical objects, combinations of geometrical and non-geometrical objects, naturally occurring structural configurations, and manmade structural configurations. A scaffold may be solid, hollow, and porous or a combination thereof. A scaffold may contain recesses, pores, openings, holes, vias, and channels or a combination thereof. A scaffold may be smooth, textured, have predetermined surface profiles and/or features. A scaffold may be intended to support one or more other materials, one or more films, a multilayer film, one type of particle, multiple types of particles etc. A scaffold may include, but not be limited to, a spine of a device and/or a framework, for example, which also supports a shell and/or a casing.

A "shell" as used herein, and throughout this disclosure, refers to a structure that is used to contain and/or surround at least partially and/or fully a number of elements within adult devices according to embodiments of the invention. A shell may include, but not be limited to, a part or parts that are mounted to, attached to, and/or surround all or part of a scaffold or scaffolds that support elements within a device according to an embodiment of the invention.

A "casing" or "skin" as used herein, and throughout this disclosure, refers to a structure surrounding a scaffold and/or shell. This includes structures typically formed from an elastomer and/or silicone to provide a desired combination of physical tactile surface properties to the device it forms part of and other properties including, but not limited to, hermeticity, liquid ingress barrier, solid particulate ingress barrier, surface sheen, and colour. A casing may include, but not limited to, a part or parts that are mounted to a scaffold or scaffolds and/or a casing or casings forming part of a device according to an embodiment of the invention.

A "resin" as used herein may refer to, but is not limited to, a solid or highly viscous substance which is typically convertible into polymers. Resins may be plant-derived or synthetic in origin.

A "polymer" as used herein may refer to, but is not limited to, is a large molecule, or macromolecule, composed of many repeated subunits. Such polymers may be natural and synthetic and typically created via polymerization of multiple monomers. Polymers through their large molecular mass may provide unique physical properties, including toughness, viscoelasticity, and a tendency to form glasses and semi-crystalline structures rather than crystals.

A "polyester" as used herein, and throughout this disclosure, refers to a category of polymers that contain the ester functional group in their main chain. This includes, but is not limited to polyesters which are naturally occurring chemicals as well as synthetics through step-growth polymerization, for example. Polyesters may be biodegradable or not. Polyesters may be a thermoplastic or thermoset or resins cured by hardeners. Polyesters may be aliphatic, semi-aromatic or aromatic. Polyesters may include, but not be limited to, those exploiting polyglycolide, polylactic acid (PLA), polycaprolactone (PCL), polyhydroxyalkanoate (PHA), polyhydroxybutyrate (PHB), polyethylene adipate (PEA), polybutylene succinate (PBS), polyethylene terephthalate (PET), polybutylene terephthalate (PBT), polytrimethylene terephthalate (PTT), and polyethylene naphthalate (PEN).

A "thermoplastic" or "thermosoftening plastic" as used herein and throughout this disclosure, refers to a category of polymers that become pliable or moldable above a specific temperature and solidify upon cooling. Thermoplastics may include, but not be limited, polycarbonate (PC), polyether sulfone (PES), polyether ether ketone (PEEK), polyethylene (PE), polypropylene (PP), poly vinyl chloride (PVC), polytetrafluoroethylene (PTFE), polyimide (PI), polyphenylsulfone (PPSU), polychlorotrifluoroethene (PCTFE or PTFCE), fluorinated ethylene propylene (FEP), and perfluoro alkoxy alkane (PFA).

An "aramid" as used herein, and throughout this disclosure, refers to an aromatic polyamide. Aramids are a class of materials fibers in which the chain molecules are highly oriented along the fiber axis, so the strength of the chemical bond can be exploited. Examples include, but are not limited to fibers distributed under brand names such as Kevlar™, Technora™, Twaron™, Heracron™, Nomex™, Innegra S™ and Vectran™ as well as nylon and ultra-high molecular weight polyethylene.

A "silicone" as used herein, and throughout this disclosure, refers to a polymer that includes any inert, synthetic compound made up of repeating units of siloxane.

An "elastomeric" material or "elastomer" as used herein, and throughout this disclosure, refers to a material, generally a polymer, with viscoelasticity. Elastomers may include, but not be limited to, unsaturated rubbers such as polyisoprene, butyl rubber, ethylene propylene rubber, silicone rubber, fluorosilicone rubber, fluoroelastomers, perfluoroelastomers, and thermoplastic elastomers.

The term "flexible," as used herein, refers to the ability of a body that is capable of being bent or flexed and refers to the ability of a body that has been subjected to an external force to return to its original size and/or shape once the external force has been removed or reduced to below a particular level. Something that is flexible can be, for example, resilient or malleable. A "flexible" material, such as a rubber for example, may be characterised by a low Young's modulus.

The term "resilient," as used herein, refers to the ability of a body that has been subjected to an external force to recover, or substantially recover, its original size and/or shape, following deformation. The term "malleable," as used herein, refers to the ability of a body that has been subjected to an external force to deform and maintain, or substantially maintain, the deformed size and/or shape. Accordingly, a malleable material supports plastic deformation. A resilient material, such as polytetrafluorethylene for example, may be characterised by a moderate Young's modulus. A rigid material, for example steel, may be characterised by a high Young's modulus but may under appropriate conditions undergo plastic deformation.

A "CAD model" as used herein may refer to, but is not limited to, an electronic file containing information relating to a component, piece-part, element, assembly to be manufactured. A CAD model may define an object within a two-dimensional (2D) space or a three-dimensional (3D) space and may in addition to defining the internal and/or external geometry and structure of the object include information relating to the material(s), process(es), dimensions, tolerances, etc. Within embodiments of the invention the CAD model may be generated and transmitted as electronic content to a system providing manufacturing according to one or more embodiments of the invention. Within other embodiments of the invention the CAD model may be derived based upon one or more items of electronic content directly, e.g. a 3D model may be created from a series of 2D images, or extracted from electronic content.

A "fluid" as used herein may refer to, but is not limited to, a substance that continually deforms (flows) under an applied shear stress. Fluids may include, but are not limited to, liquids, gases, plasmas, and some plastic solids.

A "powder" as used herein may refer to, but is not limited to, a dry, bulk solid composed of a large number of very fine particles that may flow freely when shaken or tilted. Powders may be defined by both a combination of the material or materials they are formed from and the particle dimensions such as minimum, maximum, distribution etc. A powder may typically refer to those granular materials that have fine grain sizes but may also include larger grain sizes depending upon the dimensions of the part being manufactured, the characteristics of the additive manufacturing system etc.

"Additive manufacturing" (AM) as used herein may refer to, but is not limited to, a process or processes used to create a three-dimensional object in which layers of material are formed under computer control. Commonly referred to as "3D printing" the processes of AM are currently defined in ISO/ASTM52900-15 defines several categories of AM processes although others may also be viewed as AM processes. These categories being binder jetting, directed energy deposition, material extrusion, material jetting, powder bed fusion, sheet lamination and vat photopolymerization. "3D printers" exploiting custom "inkjet" print heads are a special application of plastic extrusion known as fused deposition modelling. AM processes may be applied to plastics, ceramics, and metals. AM processes for AM sintering or melting include selective laser sintering, direct metal laser sintering, and selective laser melting whilst those for deposition may include microcasting and sprayed materials. In some instances, sacrificial and/or support materials may be employed in conjunction with AM processes to achieve the desired geometry and/or combination of materials.

"Non-additive manufacturing" (NAM) as used herein may refer to, but is not limited to, a process or processes used to create a three-dimensional object by subtractive or transformative manufacturing. NAM processes may include, but not be limited to, hydro-forming, stamping, injection molding, casting, machining, and welding.

Referring to FIG. 1 there are depicted common types of pessary type VTD according to the prior art, these being depicted as first to twenty-fourth VTDs 105A to 160B respectively in FIG. 1:

First VTD 105A cube with pull;
Second VTD 105B tandem cube;
Third VTD 110A cube with pull;
Fourth VTD 110B donut;
Fifth VTD 115A Risser;
Sixth VTD 115B Smith;
Seventh VTD 120A Gehrung with knob;
Eighth VTD 120B Gehrung;
Ninth VTD 125A Gellhorn;
Tenth VTD 125B Gellhorn;
Eleventh VTD 130A Hodge;
Twelfth VTD 130B Hodge with knob;
Thirteenth VTD 135A Smith with support and knob;
Fourteenth VTD 135B Hodge with support;
Fifteenth VTD 140A incontinence dish with support;
Sixteenth VTD 140B incontinence dish;
Seventeenth VTD 145A incontinence ring with knob;
Eighteenth VTD 145B incontinence with support;
Nineteenth VTD 150A Gehrung;
Twentieth VTD 150B ring;
Twenty-first VTD 155A incontinence ring;
Twenty-second VTD 155B incontinence ring with support and support;
Twenty-third VTD 160A Shaatz; and
Twenty-fourth VTD 160B inflatable latex.

As noted supra and evident from FIG. 1 there are a wide range of pessary options within the domain of Vaginal Therapeutic Devices (VTDs). Even considering a basic ring then we can see that there are different types:

Different thickness rings, e.g. seventeenth VTD 145A and twentieth VTD 150B wherein the fourth VTD 110B (donut) is a rather extreme version;
Rings with or without knobs, e.g. twentieth VTD 150B and twenty-second VTD 155B;
Knobs and different thicknesses and knobs, e.g. seventeenth VTD 145A and twenty-first VTD 155A; and
Rings with or without knobs and support, e.g. eighteenth VTD 145B and twenty-second VTD 155B.

Accordingly, the inventor has established a custom VTD process wherein core advantages include simplifying the fitting process as well as establishing a new paradigm between the two characteristics of support and comfort which runs counter to prior art VTDs the more support the less comfortable, less prone to expulsion during exercise, or tissue erosion over long term. Accordingly, the process established by the inventor resets this paradigm through a custom fitting and manufacturing process with a single material or multiple material VTD design allowing support to be established from a scaffold within the device whilst a shell and/or skin around the scaffold provide for increased comfort. Further, adoption of additive manufacturing processes allows the custom VTD manufacturing to be established in multiple locations with a city, state, province, country allowing improved delivery, responsiveness and supporting exploitation of custom VTDs with reduced usage duration as they exploit anti-microbial coatings, contraceptive coating, etc.

Figure 2:
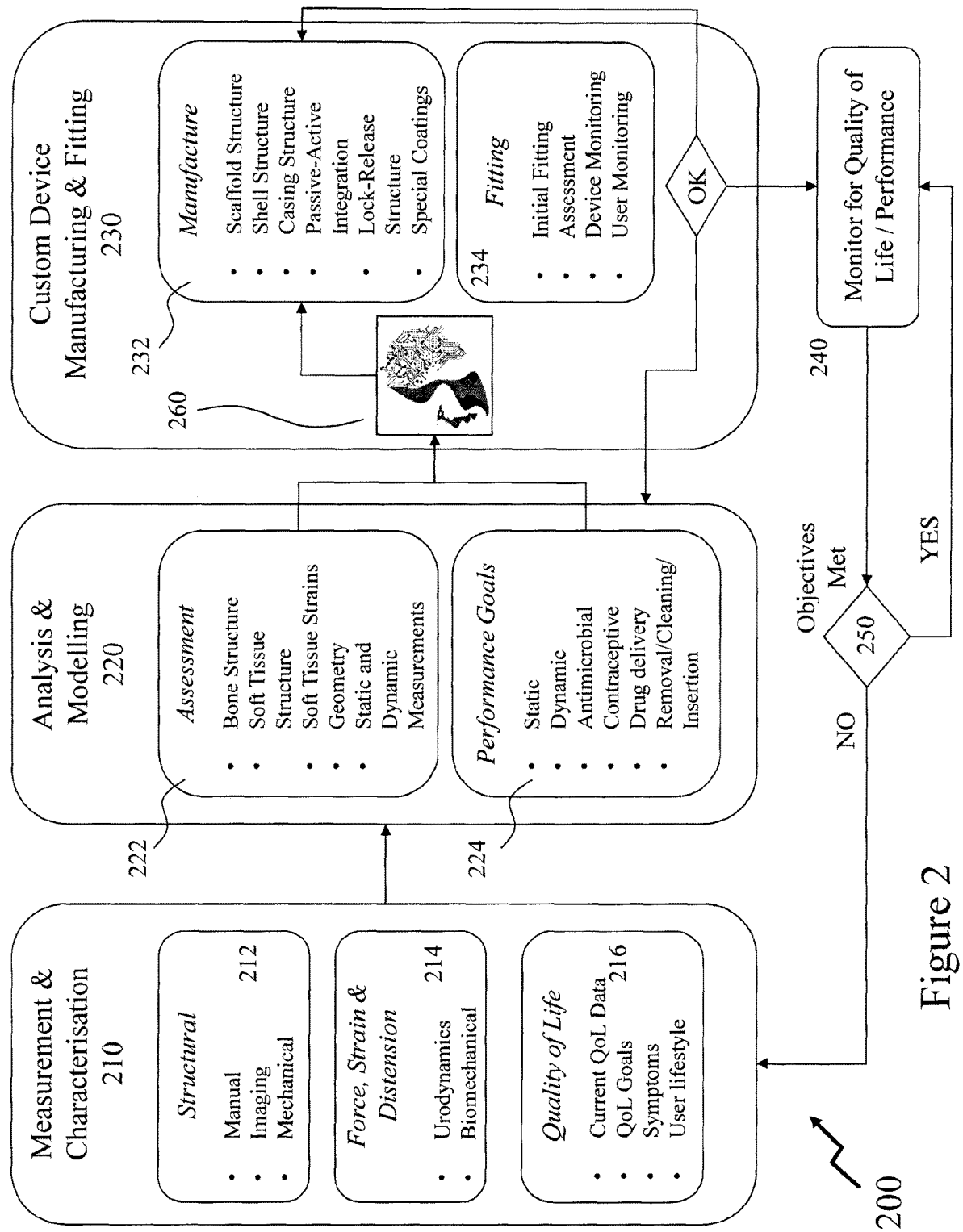
FIG. 2 depicts an exemplary process flow for providing a user with a custom USTD according to an embodiment of the invention.

Accordingly, referring to FIG. 2 there is depicted an exemplary process flow 200 for providing a user with a custom VTD according to an embodiment of the invention such that the process is reduced from a bewildering array of VTD types and dimensions to a single VTD option without significant effort from either the patient or the clinician. Accordingly, at step 210 the process begins with the step of Measurement and Characterisation (M&C) 210 before progressing to Analysis and Modelling (A&M) 220 and Custom Device Manufacturing and Fitting (CUDEMAF) 230 wherein the patient (user) is now provided and fitted with a custom VTD. Next, the process proceeds to step 240 wherein ongoing monitoring of quality of life (QoL) and performance of the VTD wherein a decision process 250 may determine whether the objectives of the VTD are being met or still being met on an ongoing basis and hence determine whether monitoring should continue or whether the process should begin again with step 210.

An ongoing monitoring and cyclic process may be appropriate for a variety of VTD use cases including, but not limited to:

changing physical characteristics of the user as they get older which may be more gradual in older users such as adults or the elderly and more rapid in younger users;

changing physiology of the user wherein additional symptoms and/or conditions manifest themselves;

changing physiology of the user in that muscles and tissue resilience, strength, compliance etc. may change; and degradation in the VTD itself.

Accordingly, as depicted M&C 210 comprises three sub-processes, these being:

Structural 212;

Force, Strain and Distension 214; and

Quality of Life 216.

Within embodiments of the invention the custom VTD may be employed in combination with other therapies and/or pharmaceutical coatings etc. in order to combine a custom VTD with regenerative medicine. Accordingly, within other embodiments of the invention a VTD according to an embodiment of the invention may exploit an energy delivery system such as infrared irradiation or ultraviolet irradiation for example. A custom VTD may also be employed in conjunction with other medical procedures and/or treatment regimens including, for example, exploitation of biological therapies including recombinant proteins, recombinant peptides and stem cells for example.

Structural 212 may comprise one or more measurements of the user's anatomy and/or measurements of the user's physical characteristics such that one or more characteristics such as the dimensions of the user's major anatomical structures, anatomical geometry, etc. are defined. For example, a Pelvic Organs Prolapse Quantification (POP-Q) may be performed, this being a standardised tool for documenting the examination findings recognised by International Continence Society (ICS) and International Urogynecological Association (IUGA). Within the POP-Q system six principle landmarks are defined to describe the degree (quantity) of Pelvic Organ Prolapse (POP). These points are located on vaginal walls and are related to the hymen which is considered a fixed point of reference. Another three landmarks may also be defined for more detailed description. The "stage" of prolapse is typically defined according to the evaluation of these points. These nine points are defined by letters Aa, Ba, C, D, Ap, Bp, GH, TVL, and PB respectively, these being:

Point Aa: This point is located in the midline anterior vaginal wall approximately 3 cm proximal from the external urethral meatus. The range of its position relative to hymen is typically from −3 cm to +3 cm.

Point Ba: The most distal position of any part in the anterior vaginal wall from the vaginal cuff or anterior vaginal fornix to Point Aa. In absence of prolapse, this point is at −3 cm and women with total uterine eversion or post hysterectomy vaginal cuff eversion would have a positive value equal to position of Point C.

Point C: The most distal edge of the cervix or vaginal cuff (hysterectomy scar) after total hysterectomy.

Point D: Represents the pouch of douglas or the location of posterior vaginal fornix. It is also a point of measurement for differentiation a suspensory failure of uterosacral-cardinal ligament "complex" from cervical elongation. Accordingly, in the absence of a cervix point D is omitted.

Point Ap: Located in the middle of posterior vaginal wall 3 cm proximal to the hymen. The range of its position relative to hymen is typically from −3 cm to +3 cm.

Point Bp: Represents the most distal position of any part in the posterior vaginal wall from the vaginal cuff or posterior vaginal fornix to point Ap.

Genital hiatus (GH): The distance between external urethral meatus and posteriori margin of the hymen.

Total Vaginal Length (TVL): The deepest length of the vagina (cm) measured when point D (or the vaginal cuff) are reduced to normal position.

Perineal Body (PB): The distance measured from posterior margin of the hymen to the mid-anal opening.

Such measurements are typically taken on valsalva except TVL. A clinician may employ a manual procedure to measure the basic six or full nine points Aa, Ba, C, D, Ap, Bp, GH, TVL, and PB respectively. This may be via the use of a ruler, swab or other mechanical measuring device. The necessary user-specific structural/anatomical parameters may also be derived from one or more imaging techniques including, but not limited to, ultrasound imaging, magnetic resonance imaging (MRI), elastography, acoustic analysis, tactile imaging, photoacoustic (optoacoustic) imaging, tomography, echocardiography, functional near-infrared spectroscopy, and electrical impedance tomography. Alternatively, mechanical based devices may be employed to perform measurements and/or support one or more transducers for one or more imaging techniques, manual processes etc. Further these measurements may be at least one intravaginal, perineal and transperineal.

Figure 12A:
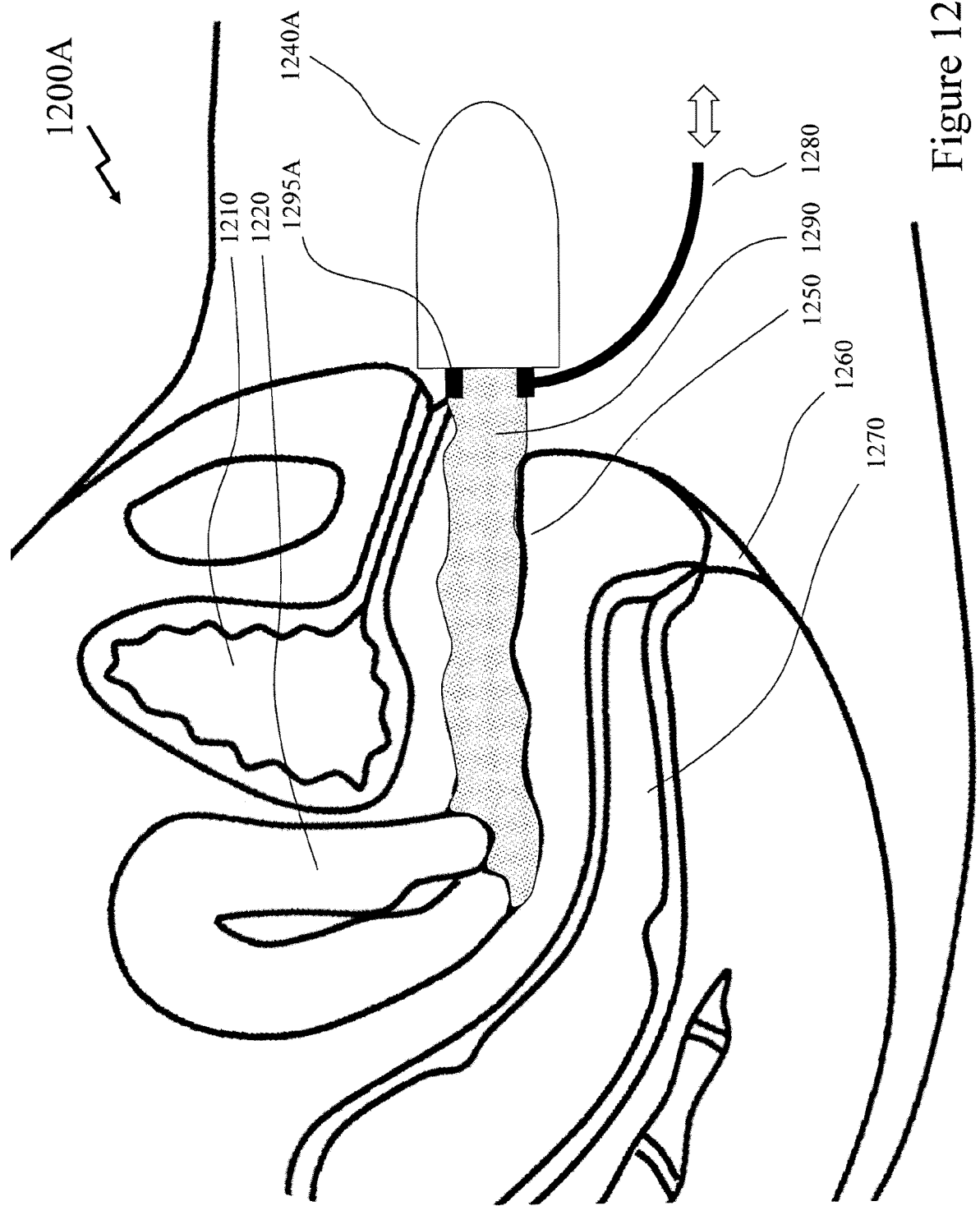
FIGS. 12A and 12B depict exemplary configurations for exploiting ultrasound for performing assessments and/or measurements according to embodiments of the invention.
Figure 12B:
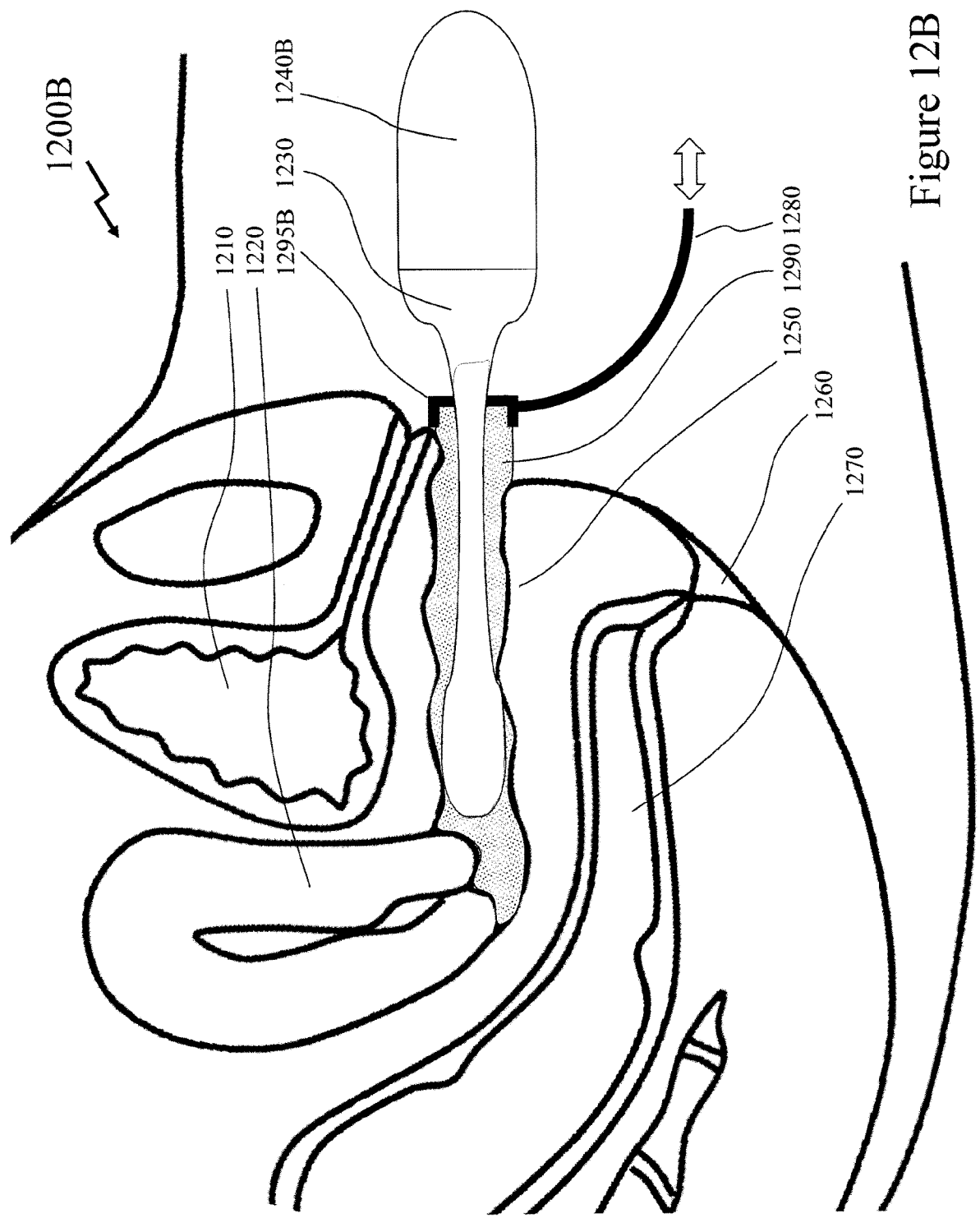

For example, within an embodiment of the invention, ultrasound imaging may be used to determine specific anatomic parameters such as cross-sectional diameter of the vagina at various cross-sections along its length. Exemplary embodiments of ultrasonic probes for performing such measurements are depicted in FIGS. 12A and 12B respectively although other configurations may be employed. Distances between various anatomical structures may also be used to determine specific anatomical parameters including but not limited to distances any of the following anatomical structures: pubic symphysis, cervix (anterior lip, posterior lip, or os), urethra, bladder neck, bladder, rectum, anus, or levator ani and other pelvic floor musculature. Importantly, mobility of the various anatomical structures may also be measured by obtaining measurements at rest and on maximum valsalva. These mobility measures help characterize the prolapsing compartment(s) and have been correlated with patient's symptoms. For example, bladder descent greater than 1 cm below the pubic symphysis on valasalva is correlated with symptoms of prolapse. In one embodiment, these data may be used to generate a prosthetic that optimally fits within the vagina and limits bladder descent and thereby minimizes patients symptoms. In addition to distances, thicknesses of the vaginal wall may also be assessed using ultrasound. Thickness data may be used to customize the mechanical properties and shape of the prosthetic device such that it minimizes the risk for vaginal ulcerations and erosions.

Force, Strain and Distension 214 may comprise one or more measurements of characteristics of the user's anatomy and/or measurements of the user's physical characteristics such as compliance/resilience of the user's tissues, the movement(s) and strength of user's musculature within the appropriate anatomical regions. These may involve mechanical and/or imaging testing discretely or in combination with other tests. Such tests may include, but not be limited to:

Vaginal manometry.
Vaginal distension with imaging from any imaging modality such as, but not limited to, ultrasound, magnetic resonance imaging (MRI), and X-ray for example.
Urodynamic measurements including, but not limited to:
Post-void residual volume wherein insertion of a urinary catheter/transducer following bladder emptying by the user is performed.
Uroflowmetry where "free" uroflowmetry measures the rate of bladder evacuation, "pressure" uroflowmetry combines rate of voiding measurements with simultaneous assessment of bladder and rectal pressures.
Multichannel cystometry which exploits a pair of pressure monitoring catheters to measure the pressure in the rectum and in the bladder to deduce the presence of contractions of the bladder wall, during bladder filling, or during other provocative maneuvers. The strength of the urethra can also be tested during this phase, using a cough or Valsalva maneuver, to confirm genuine stress incontinence.
Tactile imaging for force and strain measurements.
Elastography from ultrasound as well as other intravaginal measurements and perineal measurements.
Urethral pressure profilometry which measures the strength of sphincter contraction.
Electromyography (EMG) measurements of electrical activity in the bladder neck.
Fluoroscopy, dynamic X-ray sequences, of the bladder and bladder neck during voiding.
Intravaginal molding.

Techniques may include those identified supra and others including, but not be limited, leak point pressure, vaginal manometry, ultrasound, elastography, strain sensor array, acoustic analysis, tactile imaging, and photoacoustic (optoacoustic) imaging. The measurements performed within Structural 212 and Force, Strain and Distension 214 may be statically acquired, i.e. with the user sitting/laying/standing within a clinic or another environment and/or dynamically acquired with the user performing one or more routine aspects of their life such as Valsalva effort, walking, exercising, running, lifting, bending, etc.

In contrast to the Structural 212 and Force, Strain and Distension 214 the Quality of Life 216 is an assessment. Accordingly, Quality of Life (QoL) 216 may include, but not limited to:

Current QoL data for the user (patient) using validated questionnaires such as the Pelvic Floor Distress Inventory (PFDI) and Pelvic Floor Impact Questionnaire (PFIQ) for example;
QoL goals for the user (patient);
Symptoms experienced by the user; and
User lifestyle.

Accordingly, QoL 216 establishes baseline QoL data which may be employed subsequently for the monitoring, QoL and performance of the VTD once manufactured and employed according to embodiments of the invention. Accordingly, for one user a QoL goal may be the elimination of a symptom that occurs only during sexual activity whilst for another it may during a specific exercise, sporting activity, etc. or for another over specific periods of time and/or generally monitored etc. Additionally, the VTD in terms of being permanent, semi-permanent, or temporary is established wherein for temporary use at least the installation/removal means and/or mechanisms are established with the user. For permanent and semi-permanent the installation/removal means are geared primarily to the clinician rather than the user.

In establishing the QoL 216 a user may employ an application upon a PED and/or FED in order to track the user's (patient's) perceived QoL, to monitor and/or log even occurrences such as incontinence, pain, prolapse, pessary fall out, etc.

From M&C 210 the process proceeds to A&M 220 wherein sub-processes of Assessment 222 and Performance Goals 224 are undertaken. Within Assessment 222 the data obtained within the M&C 210 step are analysed, for example, through their entry into a human body (anatomical) model (HBM) to define a series of two-dimensional (2D) and/or three-dimensional (3D) perspectives of the user's anatomy as well as other parameters including, but not limited to:

Bone structure definition;
Soft tissue structure definition;
Soft tissue strains;
Relative positions of bones and/or soft tissues and/or surrounding organs;
Static body position in one or more position such as supine, sitting, and standing, for example;
Dynamic body position such as walking, bending, squatting, lifting, and jogging, for example;
Dynamic forces and structural measurements; and
Dynamic pressure from activities such as cough and Valsalva, for example.

Within Performance Goals 224 the QoL 216 data is established as specific static and dynamic performance goals for the VTD. These may include, but not be limited to, whether the VTD is to address urinary and/or fecal incontinence, number of episodes and volume, degree of comfort level required, will or can the user perform self-removal/cleaning/insertion etc., will this require periodic visits to a physician or clinic, and will any coatings require the user periodically dispose of the VTD and use a new VTD. Additionally, additional characteristics may be established with respect to providing an antimicrobial coating, providing controlled pharmaceutical product release(s) such as combinations of estrogen and progesterone for contraception, spermicide, proteins, regenerative medicine(s) or other drugs for the user. These together with the data from Assessment 222 are employed in defining the custom VTD for the user in terms of physical geometry, e.g. dimensions of any ring structure, knob, support etc. Additionally, the mechanical properties of the custom VTD are defined in respect of the flexibility, dimensional stability, installation/removal means, physical characteristics of the VTD such as smooth/contoured surfaces and/or regions, etc. as well as other aspects such as any locking and/or release mechanisms.

Based upon the established mechanical and physical requirements together with appropriate aspect of the QoL requirements the process in Custom Device Manufacturing and Fitting (CUDEMAF) 230 proceeds with a sequence comprising Manufacture 232 and Fitting 234. The accumulated data from the Analysis & Modelling 220 as defined within Assessment 222 and Performance Goals 224 is coupled to an Artificial Intelligence (AI) Engine 260 which employs a plurality of algorithms which may exploit one or more approaches including, but not limited to, those based on symbol manipulation, cognitive simulation, logic-based programming, anti-logic programming, natural language processing, knowledge based, sub-symbolic, embodied intelligence, computational intelligence and soft computing, and statistical either individually or in combination such as within methodologies such as the intelligent agent, multiple interacting agents in a multi-agent system, and a hybrid intelligent system.

The AI Engine 260 may employ a hierarchal control system to bridge between sub-symbolic AI and symbolic AI. Tools exploited by the AI Engine 260 may include, but are not limited to, search and optimization, evolutionary computation, swarm intelligence algorithms, evolutionary algorithms, logic programming, fuzzy systems, subjective logic, default logics, non-monotonic logics, circumscription, probabilistic methods for uncertain reasoning, Bayesian networks, Hidden Markov models, utility theory, decision theory, Kalman filters, dynamic decision networks, classifiers and statistical learning methods, classifiers, neural networks, kernel methods, k-nearest neighbour algorithm, naïve Bayes classifier, decision tree, neural networks, artificial neural networks, acyclic or feedforward neural networks, recurrent neural networks, perceptrons, multi-layer perceptrons, radial basis networks, backpropagation networks, deep feedforward neural networks, convolutional neural networks, reinforcement learning, deep recurrent neural networks, recurrent neural networks, and gradient descent training.

Within Manufacture 232 the custom VTD is defined in respect of the materials providing its physical geometry with the desired mechanical properties as well as external characteristics. Accordingly, the custom VTD may be defined by one or more aspects including, but not limited to:

Scaffold structure by dimension(s), material(s) etc.
Shell structure by dimension(s), material(s) etc.
Casing structure by dimension(s), property or properties, material(s).
Passive-active integration such as is VTD passive or does it embed sensor(s), control and/or data logging circuitry, wireless interface(s) etc.
Lock-release structure.
Coatings.

Accordingly, a CAD model is established from which the Manufacture 232 process is undertaken. Within an embodiment of the invention an initial CAD model may be established by combining three-dimensional (3D) modelling with computational fluid dynamics (CFD), finite element analysis (FEA), and/or multi-organ free-body diagram models. The CAD model may be simplified to reduce the required computational power and complexity of the processing applied prior to the AI Engine 260 executes. The AI Engine 260 may process based upon this initial pre-processing solely or may apply the pre-processing to a more complete human body (anatomical) model and VTD model in order to define the VTD design, CAD, and materials requirements. Optionally, the pre-processing may be bypassed where appropriate levels of computing resources are available. Within an embodiment of the invention the AI Engine 260 generates the design of the VTD in dependence upon the computational modelling, FEA analysis, 3D modelling either individually or in combination.

Accordingly, a VTD as designed and manufactured may range from a passive VTD through to an active VTD, with lock-release structure, anti-microbial coating, and wireless interface for transmitting and logging data relating to the user.

Within Fitting 234 the custom VTD is provided to the user and either fitted by themselves, e.g. for temporary use VTD that the user will insert/remove as desired, or by a clinician, e.g. semi-permanent or permanent use. At this point one or more assessments may be carried out such as outlined previously in respect of Structural 212 and/or Force, Strain and Distension 214 whereby, for example, mechanical, imaging, static and/or dynamic assessment etc. are performed to assess the VTD fit against the target design/user physiology etc. Optionally, the Structural 212 and/or Force, Strain and Distension 214 may be device based assessments and/or non-device based (e.g. clinical) assessments. This stage may also include device monitoring, e.g. via internal sensors to the VTD, as well as user monitoring, e.g. by personally noting performance of the VTD etc. Based upon these results a determination is made as to whether the VTD meets the initial requirements wherein if yes, the process proceeds to step 240. If not, then the process proceeds to loop back to either A&M 220 or CUDEMAF 230 according to the nature and/or complexity of the modifications/amendments required.

In step 240 the user employs the VTD on an ongoing basis wherein device monitoring, e.g. via internal sensors to the VTD, as well as user monitoring, e.g. by personally noting performance of the VTD etc. are performed wherein periodically this data is employed in determining whether the objectives for the VTD were met in step 250. If yes, then the process loops back to step 240 otherwise it proceeds back to step 210. For example, a young user may require multiple VTDs within the space of a few years/decade during their childhood, adolescence, puberty, etc. with evolving dimensions and requirements whereas an elderly user may require a single adjustment or no adjustment according to their circumstances.

Within the description supra monitoring of the user has been described and discussed with respect to the fitting, assessment, and performance monitoring of a VTD or USTD according to an embodiment of the invention. Whilst this may exploit one or more sensors embedded within the body of the VTD and/or USTD or upon its surface as discussed below it would be evident that the assessment may employ and exploit data acquired from a range of other wearable devices and biometric sensors in order to enhance, for example, the assessment, fitting, and monitoring of VTDs and/or USTDs according to embodiments of the invention wherein the additional data obtained, e.g. biometric data, environmental data, activity data, body position data, etc., provides correlation data and/or additional data For example, a patient suffering UI may experience this when bent over and/or walking but not during sitting and/or being prone. Further, the ongoing acquisition of data from a range of other wearable devices and biometric sensors may also be employed in association with or without sensors within the VTD and/or USTD to provide ongoing quality of life (QoL) data to assess the effectiveness of the VTD and/or USTD.

Figure 3:
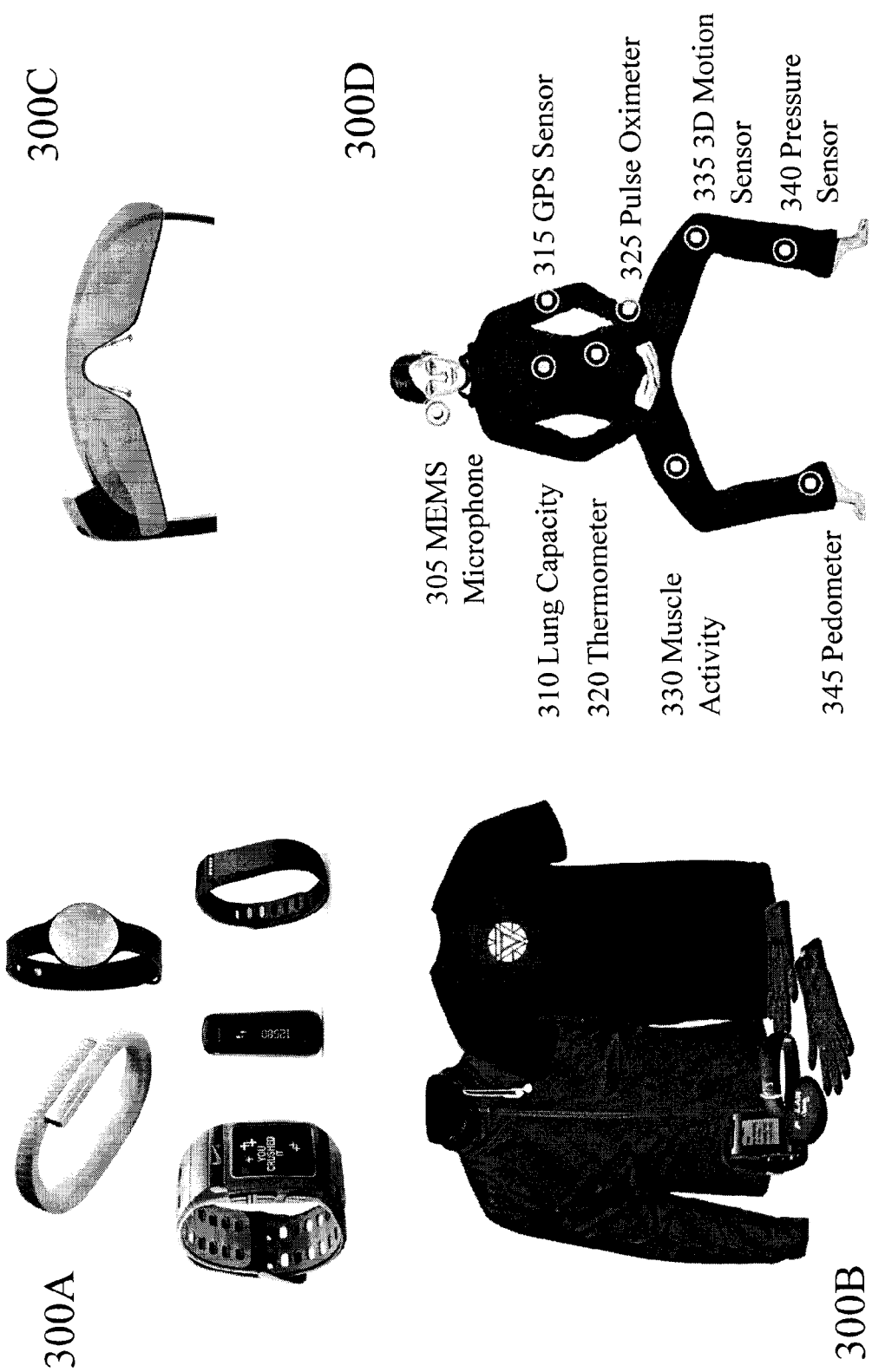
FIG. 3 depicts examples of wearable devices and biometric sensors as may be associated with the assessment, fitting, and monitoring of USTDs within embodiments of the invention.

Accordingly, referring to FIG. 3 there are depicted in first to third images 300A to 300C examples of current wearable devices as may be associated with and/or implement embodiments of the invention including, but not limited to, smart watches, activity trackers, smart shirts, pressure sensors, and blood glucose sensors that provide biometric data relating to the user of said wearable device(s). Within first image 300A examples of wearable devices are depicted whilst within second image 300B examples of smart clothing are depicted. Third image 300C depicts an example of a wearable device presenting information to a user in contrast to the devices/clothing in first and second images 300A and 300B respectively that collect contextual, environmental, and biometric data.

Smart clothing may be made from a smart fabric and used to allow remote physiological monitoring of various vital signs of the wearer such as heart rate, respiration rate, temperature, activity, and posture for example or alternatively it refers to a conventional material with embedded sensors. A smart shirt may, for example, record an electrocardiogram (ECG) and provide respiration through inductance plethysmography, accelerometry, optical pulse oximetry, galvanic skin response (GSR) for skin moisture monitoring, and blood pressure. Information from such wearable devices may be stored locally or with an associated device, e.g. smartphone, as well as being stored remotely within a personal server, remote cloud based storage, etc. and communicate typically via a wireless network such as Bluetooth, RF, LAN, or cellular network although wired interfaces may also be provided, e.g. to the user's smartphone, laptop, or dedicated housing, allowing data extraction as well as recharging batteries within the wearable device.

Also depicted in FIG. 3 is fourth image 300D relating to sensors providing/exploiting biometric data relating to a user. For example, within fourth image 300D a user's smart clothing provides data from sensors including, but not limited to, those providing acoustic environment information via MEMS microphone 305, user breathing analysis through lung capacity sensor 310, global positioning via GPS sensor 315, their temperature and/or ambient temperature via thermometer 320, and blood oxygenation through pulse oximeter 325. These are augmented by exertion data acquired by muscle activity sensor 330, motion data via 3D motion sensor 335 (e.g. 3D accelerometer), user weight/carrying data from pressure sensor 340 and walking/running data from pedometer 345. These may be employed in isolation or in conjunction with other data communicated to a body area aggregator, e.g. PED or dedicated wearable computer. Accordingly, it would be apparent that a user may have associated with themselves one or more sensors, either through a conscious decision, e.g. to wear a blood glucose sensor or an unconscious decision, e.g. carrying an accelerometer within their cellphone. Further historic data from the remote storage and/or the Internet may also be used in conjunction with the data acquired in the manners described above in order to, for example, put the current data into context, aid in decision making, determine normal or abnormal data and/or events. Accordingly, this data may be used with other sensor data, such as from sensors embedded within smart underwear or smart underwear liner, a vaginal monitoring device etc. to establish activity and lifestyle data to associate to the data acquired within the M&C 210 stage of the user's assessment.

Within embodiments of the invention the user may be provided with a special VTD style device design to fit within the vagina and monitor aspects of the user such as muscle movement, muscle contraction/relax, bladder leakage, rectal leakage etc. Similarly, a liner for the user's underwear or an item of underwear may further incorporate sensors to determine whether an event has occurred and/or the magnitude of the event where the VTD is intended to address a QoL issue such as incontinence for issue.

FIG. 4 depicts different VTD and electronic device configurations as may be supported by embodiments of the invention where the user either employs a VTD with sensors during an assessment phase or during extended use post custom VTD acquisition for ongoing assessment and/or monitoring. Accordingly, there are depicted first to fourth configurations 400A to 400D respectively in respect of different VTD and electronic device configurations as may be supported by embodiments of the invention. Accordingly, a PED 405, which in other configurations not depicted may be a FED, is wirelessly coupled to a network, such as a global communications network (e.g. the Internet or World Wide Web) and therein active VTD combinations comprising first/second elements 410A/410B and fourth/fifth elements 420A/420B respectively either in isolation or with additional devices 480 and 490 respectively in first to third configurations 400A to 400C. As depicted:

First element 410A comprising first electronics 430A and first sensor 440A, wherein the first electronics 430A provides a wireless interface to PED 405 and a wired interface to fourth element 420A as well as receives signals from first sensor 440A;

Second element 410B comprising second electronics 430B and first sensor 440A, wherein the electronics 430B provides a wireless interface to PED 405 and a wireless interface to fifth element 420B as well as receives signals from first sensor 440A;

Fourth element 420A comprising fourth electronics 450A and second/third sensors 460A/470A, wherein the electronics 450A provides a wired interface to first element 410A as well as receives signals from second/third sensor 460A/470A;

Fifth element 420B comprising fifth electronics 450B and second/third sensors 460A/470A, wherein the electronics 450B provides a wireless interface to first element 410B as well as receives signals from second/third sensors 460A/470A.

Accordingly, in first configuration 400A the PED 405 communicates with the first element 410A which is coupled via wired interface to second element 410B. In second configuration 400B the wired interface between first/fourth elements 410A/420A is replaced with a wireless interface between second/fifth elements 410B/420B respectively. Within third configuration 400C the second configuration 400B is extended with additional device 480 coupled to the PED 405, such as a wearable device providing biometric data, for example. Within fourth configuration 400D third element 410C communicates directly to network 100 via third electronics 430C which also receives signals from first sensor 440A as well as wireless interfaces to fifth element 420B as well as additional devices 480/490. Within fourth configuration 400D the device 490 may provide biometric data to third and fifth elements 410C and 420B whilst device 480 only provides data to third element 410C.

Within embodiments of the first/second/third elements 410A/410B/410C and fourth/fifth elements 420A/420B may be elements of the same VTD for a user or elements of two or more devices including a VTD for use by a user. In other embodiments of the invention each element may be in wireless communication with the PED 405 or a FED or the network rather than a single element. In some embodiments of the invention the functionality provided by an element may be varied automatically as the PED 405 determines communication to another element as being present. It would be evident that in embodiments presented with wireless interfaces that these may be replaced with wired interfaces and vice-versa. Optionally, within other embodiments of the invention the fourth/fifth elements 420A/420B may be omitted with the VTD comprising a single element. Optionally, the first/second/third elements 410A/410B/410C and fourth/fifth elements 420A/420B may be elements of the same physical VTD wherein the wireless or wired interface provides for the VTD to meet the physical-performance requirements.

Optionally, the data acquired from a VTD may be stored within a profile associated with the user with secure/encrypted communications to/from the VTD and the user's PED and/or FED as well as between the VTD and/or PED/FED with a remote server. This profile may further include data acquired during Measurement & Characterisation 210, Analysis and Modelling 220 and Custom Device Manufacturing & Fitting 230 as described and depicted in FIG. 2. Such a profile may be accessed via security methods as known in the art by a physician, clinician, custom VTD manufacturer, etc.

Figure 5A:
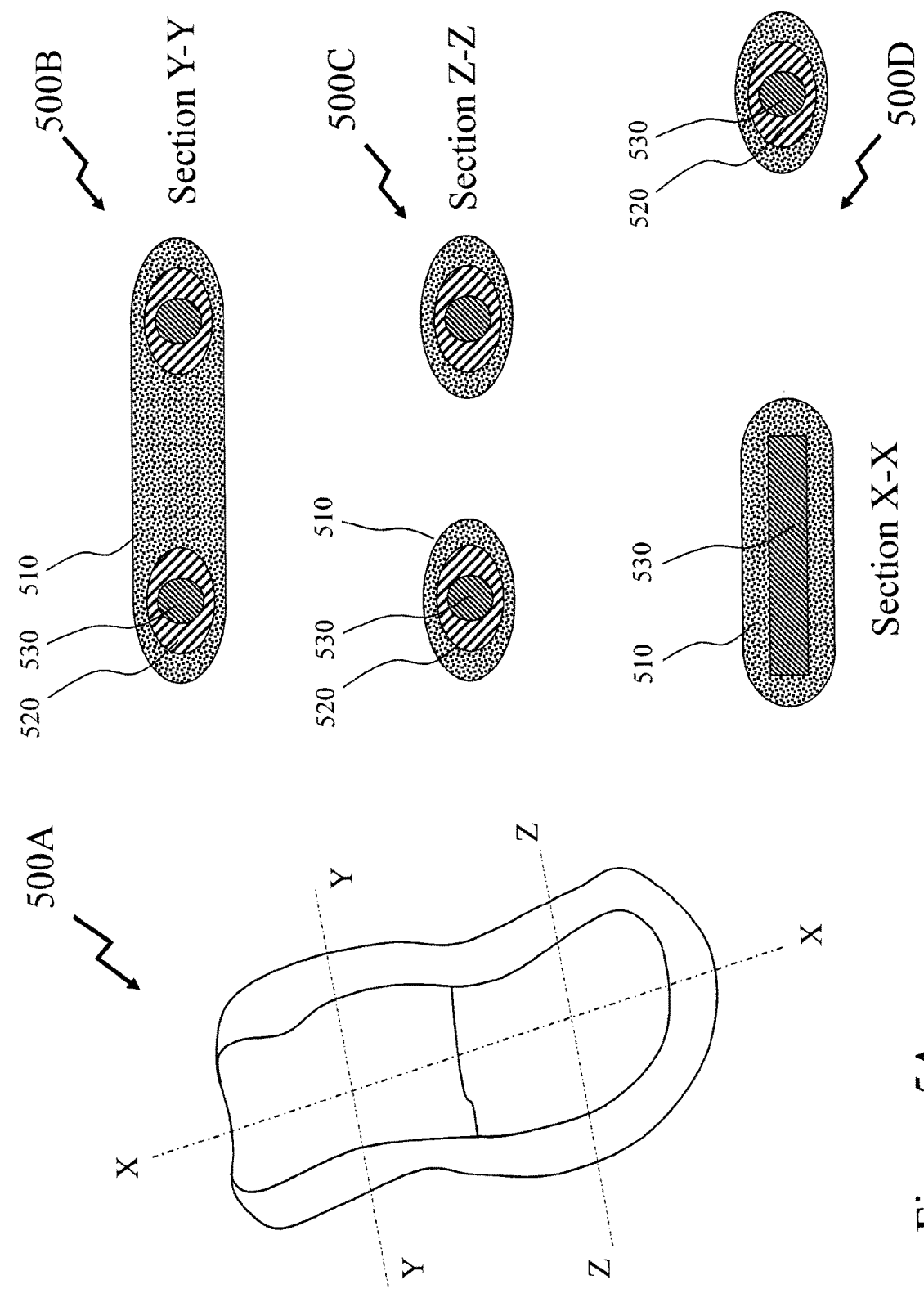
FIGS. 5A to 5C depict exemplary USTDs according to embodiments of the invention.

Referring to FIG. 5A there is depicted an exemplary VTD according to an embodiment of the invention in first to fourth views 500A to 500D respectively of a Hodge type VTD. These being:

First view 500A which is perspective 3D view;
Second view 500B which is a cross-section along section line Y-Y;
Third view 500C which is a cross-section along section line Z-Z; and
Fourth view 500D which is a cross-section along section line X-X.

Accordingly, the VTD depicted in FIG. 5A comprises a

Scaffold 530 which provides, typically, mechanical integrity and determines characteristics such as rigidity, flexibility etc. as this may be, for example, a metal or alloy within embodiments of the invention, a high strength polymer within other embodiments of the invention, an aramid fiber within embodiments of the invention, or a reinforced fiber composite within other embodiments of the invention.

Shell 520 which provides additional characteristics such as compliance of the exterior of the VTD and may be formed from a foam, plastic, etc. for example.

Casing 510 which provides the exterior body contact portion of the VTD which may be formed using a silicone for example.

Figure 5B:
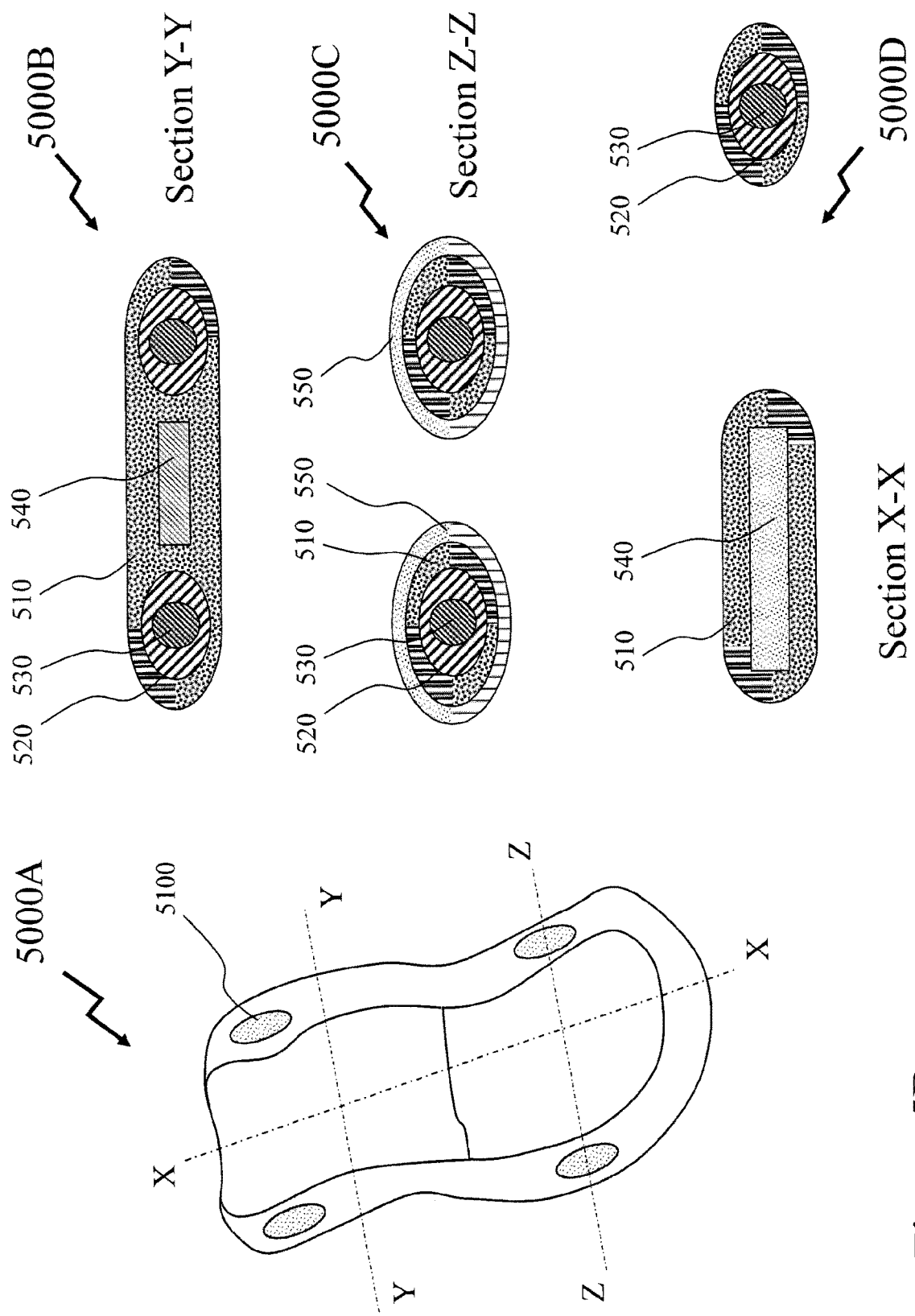

FIG. 5B there is depicted an exemplary VTD according to an embodiment of the invention in first to fourth views 5000A to 5000D respectively. As such a Hodge type VTD is depicted with support. The first to fourth views 5000A to 5000D respectively being:

First view 5000A which is perspective 3D view;
Second view 5000B which is a cross-section along section line Y-Y;
Third view 5000C which is a cross-section along section line Z-Z; and
Fourth view 5000D which is a cross-section along section line X-X.

Accordingly, the VTD depicted in FIG. 5B comprises a

Scaffold 530 which provides, typically, mechanical integrity and determines characteristics such as rigidity, flexibility etc. as this may be, for example, a metal or alloy within embodiments of the invention, a high strength polymer within other embodiments of the invention, an aramid fiber within embodiments of the invention, or a reinforced fiber composite within other embodiments of the invention. Optionally, the material(s) for the scaffold may be a pre-defined boundary condition within the design process as the material or materials may offer benefits such as biocompatibility, cost, compatibility with manufacturing processes, or compatibility with other materials such as those for the shell, casing etc.

Shell 520 which provides additional characteristics such as compliance of the exterior of the VTD and may be formed from a foam, plastic, etc. for example.

Casing 510 which provides the exterior body contact portion of the VTD which may be formed using a silicone for example.

Electronics 540 which provides for control, power, data logging etc. of sensors 5100 deposed at points along the VTD.

Sensor 550 may be a thin film sensor or a thick film sensor.

Sensors 5100 may be a single sensor, a plurality of sensors of the same type, single sensors of a plurality of types, or multiple sensors of a plurality of types. Whilst four sensors 5100 are depicted in FIG. 5B it would be evident that a single sensor may be employed, as may two, three, five, etc. Within FIG. 5B the sensor 5100 is depicted as a thin or thick film surrounding the scaffold, shell, and casing whilst within other embodiments of the invention the casing may be missing where the sensor 5100 is deployed. Optionally, the sensor 5100 may be embedded within the casing and shell. Optionally, the scaffold 530 and shell 520 may be formed to provide channels, grooves, etc. for electrical connections between the sensors 5100 and electronics 540. Examples of the sensor 5100 may include, but are not limited to, a temperature dependent resistor, a humidity dependent resistor, a strain dependent resistor, strain dependent capacitor, strain dependent inductor, and piezoelectric pressure sensor.

Optionally, a variant of the VTD according to an embodiment of the invention may have an array of sensors allowing the VTD to act as a measurement device for use during the Measurement & Characterisation 210 as depicted in FIG. 2 with an array of sensors, e.g. 4, 8, 16, etc. Such a sensor embedded VTD may be employed in data acquisition for a "Vaginal Tactile Imaging" system providing an array of force measurements.

Figure 5C:
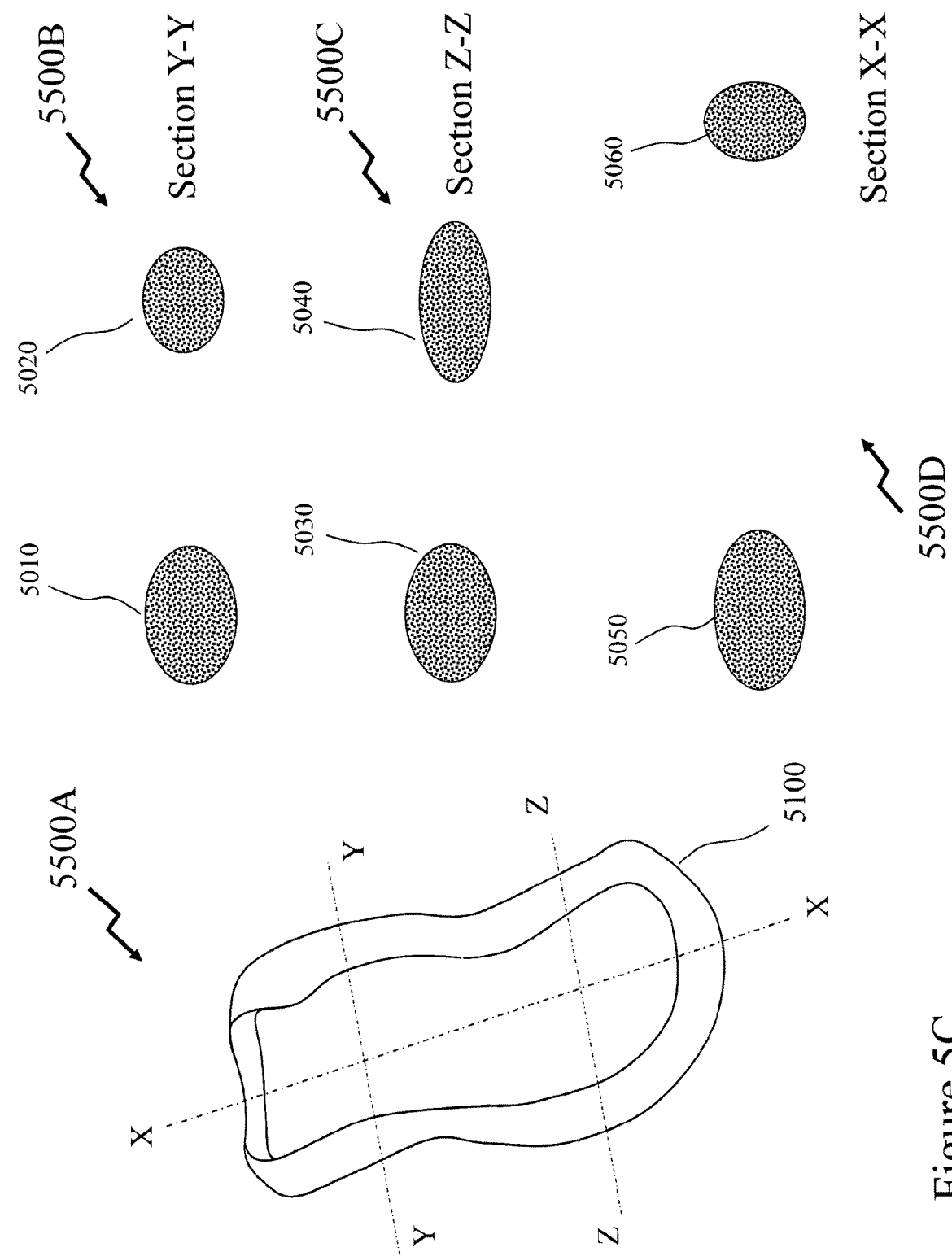

Now referring to FIG. 5C there is depicted an exemplary VTD according to an embodiment of the invention in first to fourth views 5500A to 5500D respectively. As such a Hodge type VTD is depicted with support. The first to fourth views 5500A to 5500D respectively being:

First view 5500A which is perspective 3D view;
Second view 5500B which is a cross-section along section line Y-Y;
Third view 5500C which is a cross-section along section line Z-Z; and
Fourth view 5500D which is a cross-section along section line X-X.

Accordingly, the VTD depicted in FIG. 5C comprises a custom shaped ring 5100 formed from a single material which provides the required mechanical integrity and other characteristics required to perform its function. As depicted within second to fourth views 5500B to 5500D respectively the ring 5100 has first to sixth cross-sections 5010 to 5060 respectively. These cross-sections are determined by the AI Engine in response to the accumulated data, e.g. that obtained from the Analysis & Modelling 220 as defined within Assessment 222 and Performance Goals 224. Accordingly, these first to sixth cross-sections 5010 to 5060 respectively are defined in dependence upon the patient's (user's) physiological and physical characteristics.

Figure 6A:
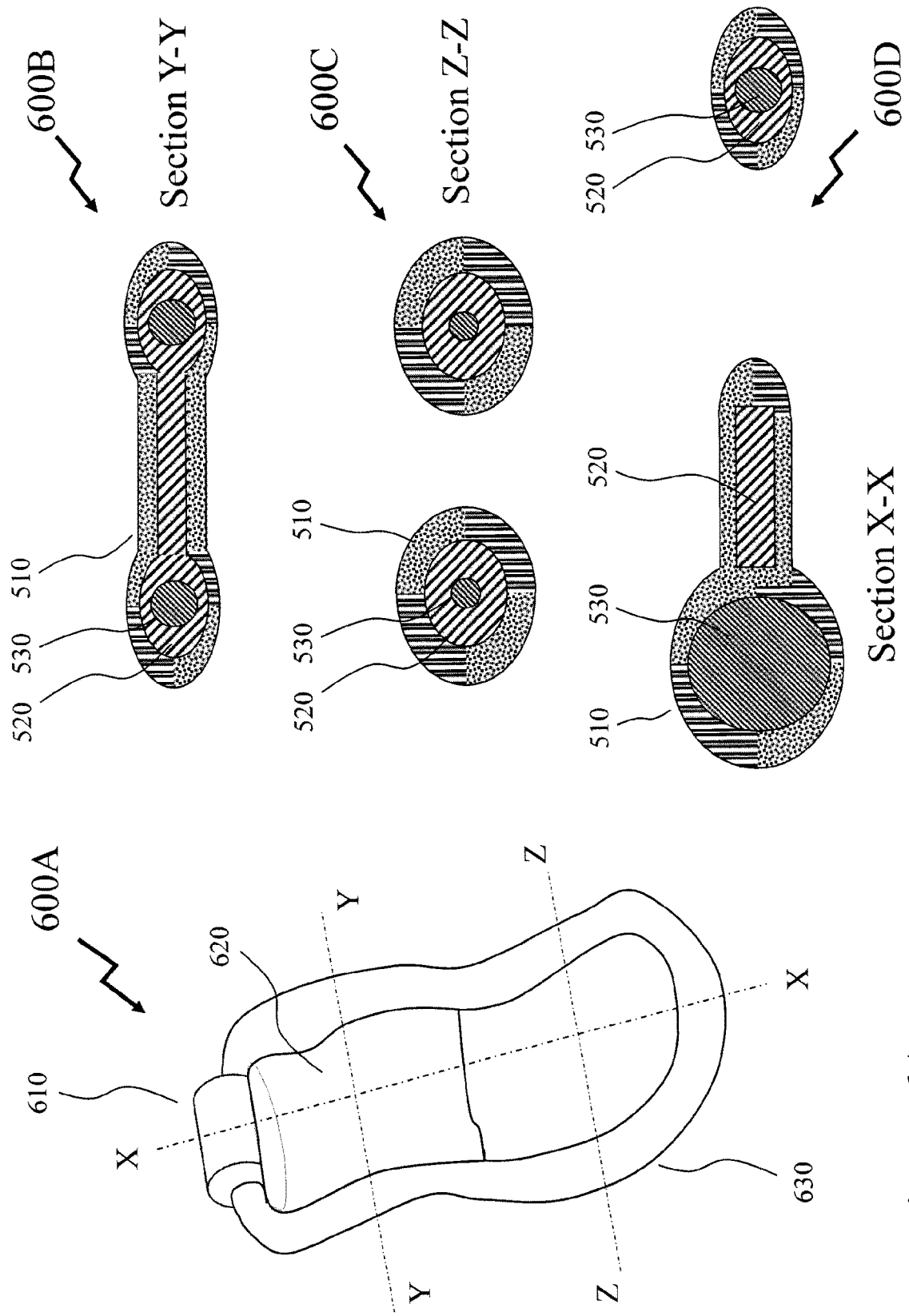
FIGS. 6A to 6C depict exemplary USTDs according to embodiments of the invention.

Now referring to FIG. 6A there is depicted an exemplary VTD according to an embodiment of the invention in first to fourth views 600A to 600D respectively. These being:

First view 600A which is perspective 3D view;
Second view 600B which is a cross-section along section line Y-Y;
Third view 600C which is a cross-section along section line Z-Z; and
Fourth view 600D which is a cross-section along section line X-X.

Accordingly, the VTD depicted in FIG. 6A is constructed from three structures, a scaffold 530, a shell 520, and a casing 510. The scaffold 530 provides, typically, mechanical integrity and determines characteristics such as rigidity, flexibility etc. as this may be, for example, a metal or alloy within embodiments of the invention, a high strength polymer within other embodiments of the invention, an aramid fiber within embodiments of the invention, or a reinforced fiber composite within other embodiments of the invention. The shell 520 provides additional characteristics for the VTD such as compliance of the exterior of the VTD and may be formed from a foam, plastic, etc. for example. The casing 510 provides the exterior body contact portion of the VTD which may be formed using a silicone for example to provide a biocompatible exterior to the VTD.

As depicted the VTD comprises a bladder support knob 610, a support 620, and a ring 630. The substantially oval ring 630 fits around the user's cervix whilst the bladder support knob 610 engages from within the vagina against the user's balder. The support 620 helps the bladder support knob 610 maintain the required pressure to provide the support. As depicted the scaffold 530 varies in geometry between cross-section Y-Y in second view 600B where the support 620 is disposed between the ring 630 portions. The support 620 being formed by the shell 520 within the casing 510. As evident from cross-section Z-Z in third view 600C the scaffold 530 is smaller within the portion of the ring 630 that fits around the cervix than the portion with the support 620. At the same time the shell 520 and casing 510 are also thicker within the portion of the ring 630 absent the support 620. In contrast, the bladder support knob 610 is larger and formed from the scaffold 530 with only casing 510 surrounding it whilst the support portion is formed from shell 520 and casing 510. The dimensions of each portion of the VTD are established in dependence upon the user's physiology and incontinence episode characteristics.

Figure 6C:
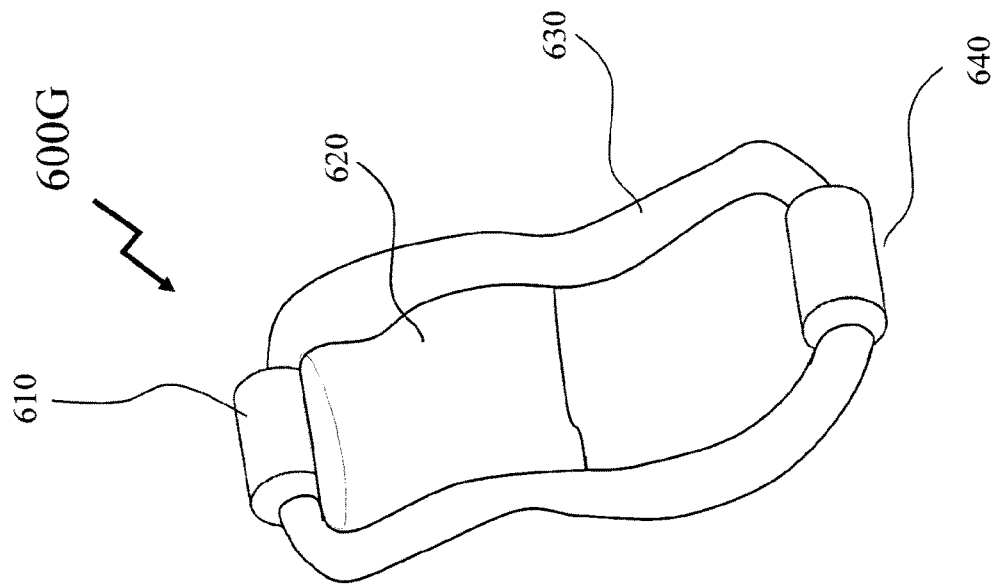
Figure 6B:
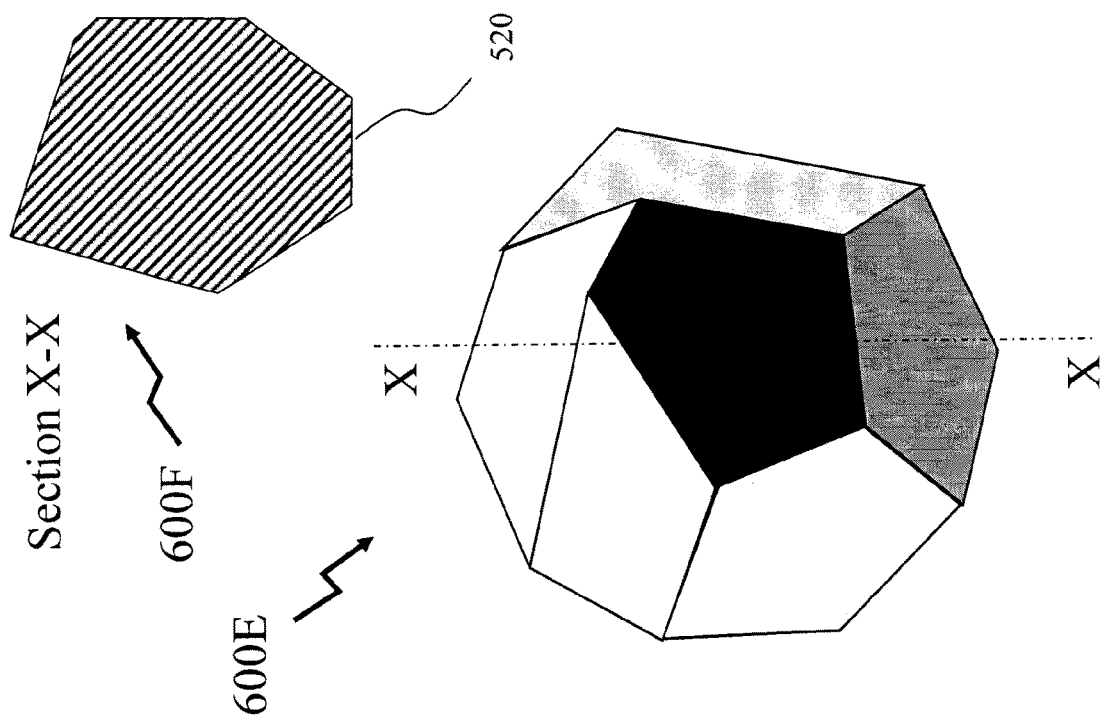

Now referring to FIG. 6B there is depicted an irregular VTD in first image 600E for a user with a stage 3-4 prolapse. In contrast to a prior art VTD for user with such a prolapse the geometry of the irregular VTD 600E is established uniquely in dependence upon the physical characteristics of the user and the physiology of the stage 3-4 prolapse. Cross-section X-X depicted in second image 600F indicates that the irregular VTD is formed from a single material, shell 520. Optionally, the irregular VTD may for formed with a casing 510 around the shell 520. As with the other embodiments of the invention described in respect of FIGS. 5A-5C respectively the irregular VTD may be formed from a combination of materials, namely shell, scaffold, skin, multiple scaffolds, multiple shells, multiple skins etc.

Referring to FIG. 6C there is depicted a VTD with bladder support knob 610, a support 620, and ring 630. However, the ring 630 now also has a retainer knob 640 disposed at the end distal to the bladder support knob 610 which is designed to improve retention of the VTD when inserted. Again, the design of the ring 630, bladder support knob 610, and retainer knob 640 are designed based upon the user's specific physical and physiological characteristics.

Within embodiments of the invention a VTD may comprise:

A scaffold 530 only;
A scaffold 530 with a casing 510;
A scaffold 530 with a shell 520;
A scaffold 530 with a shell 520 and casing 510;
A shell 520 with a casing 510;
A shell 520; and
A casing 510.

Whilst within FIGS. 5A-5C, 6A-6C and 7 respectively a single scaffold, shell and casing have been described and depicted embodiments of the invention may exploit multiple scaffolds and/or shells and/or casings in different combinations including within the same VTD according to the requirements of the custom VTD. Optionally, multiple scaffolds and/or casings and/or skins may be defined within different regions of the VTD.

Within some embodiments of the invention one or more materials employed in the VTD may be electroactive polymers allowing the VTD to dynamically adjust over a predetermined range relative to its original manufactured dimensions. Accordingly, a dynamic VTD may be implemented wherein QoL data, a force measurement, a geometric measurement, etc. may be employed to trigger an adjustment in the VTD dimensions thereby adjusting the shape and/or force it applies to the user wherein subsequent data acquisition indicates whether the VTD has improved the user's QoL.

Figure 7A:
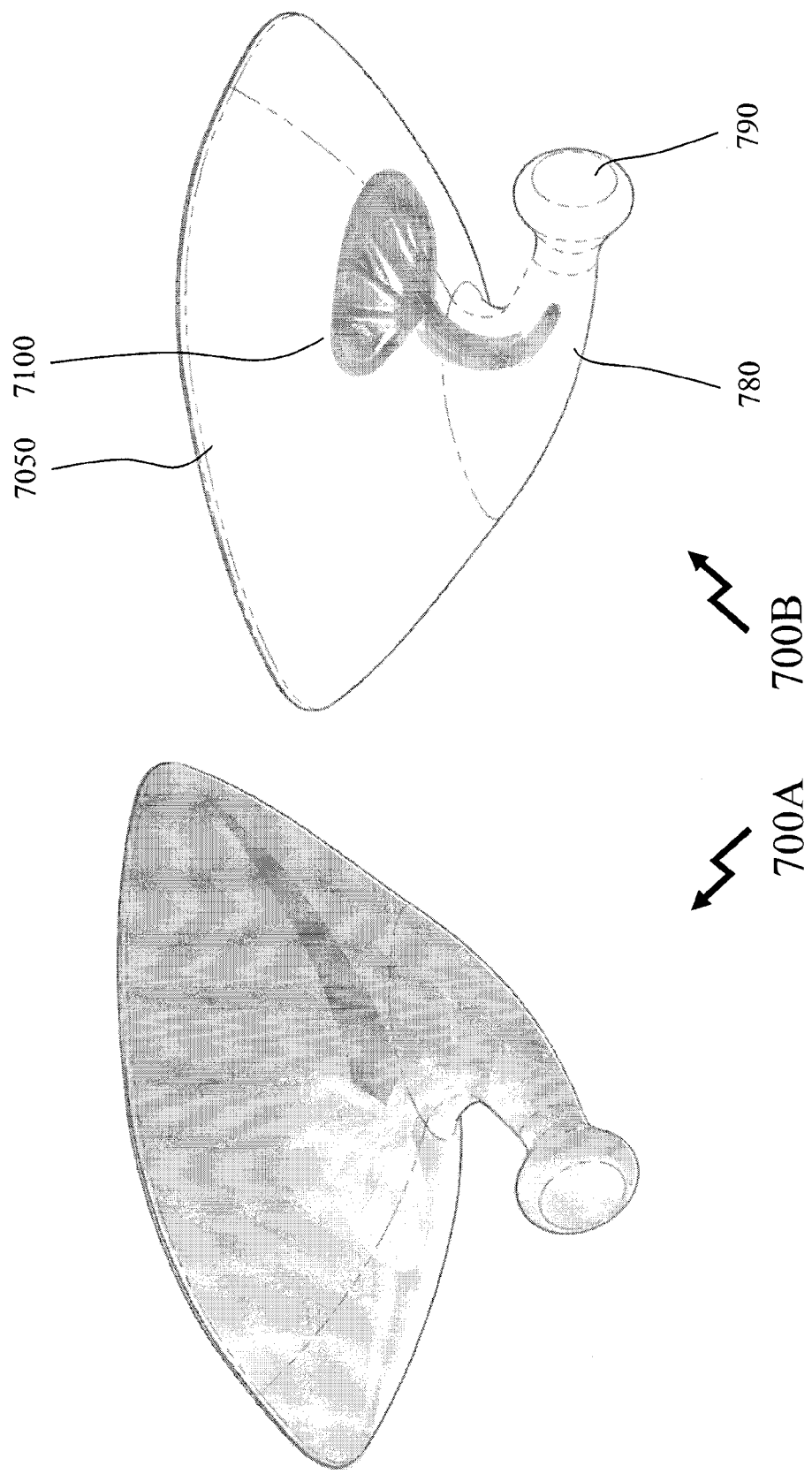
FIGS. 7A to 7C depict exemplary USTDs according to embodiments of the invention.
Figure 7B:
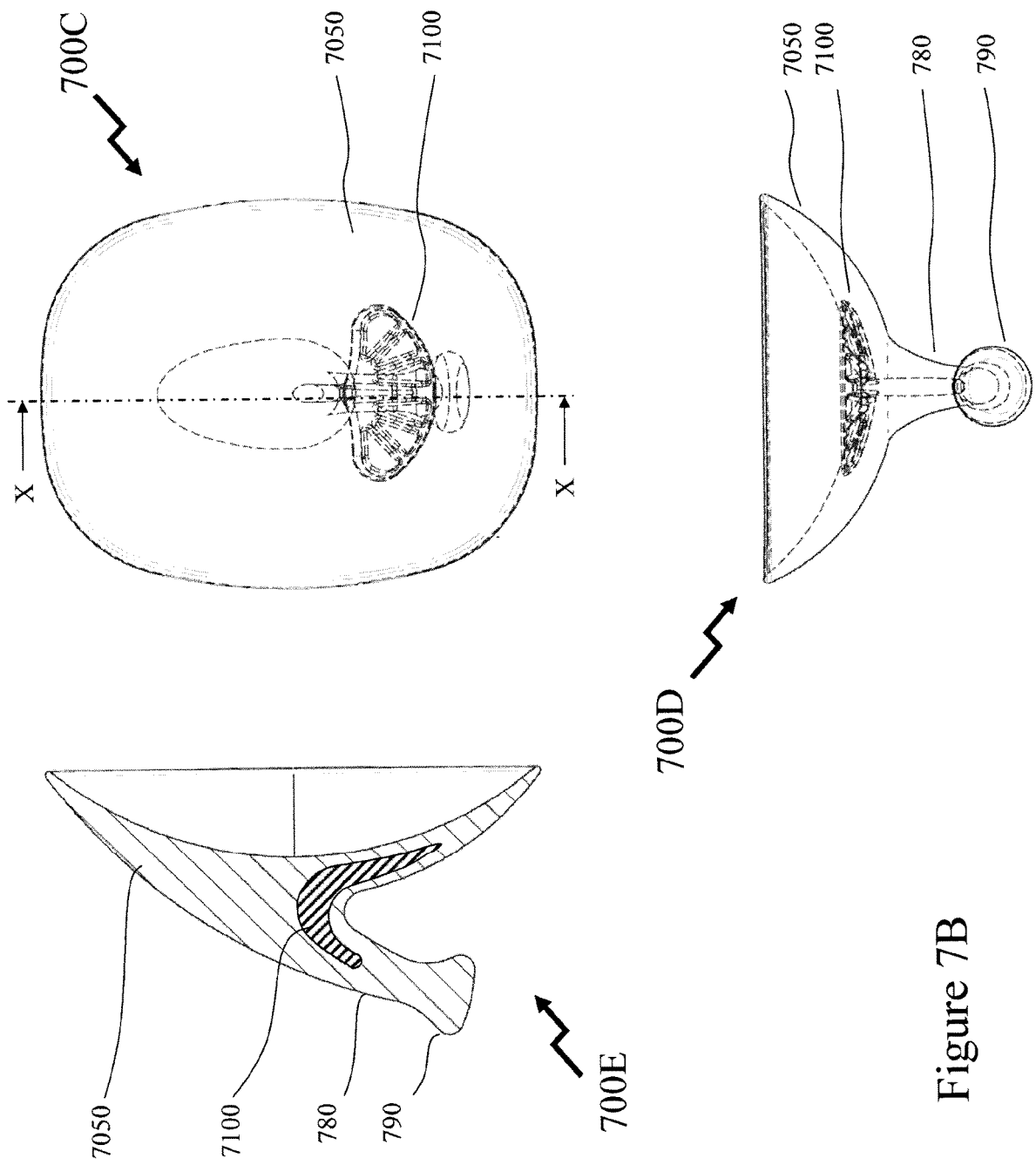

Referring to FIGS. 7A and 7B respectively there are depicted first to fifth images 700A to 700E respectively of a VTD according to an embodiment of the invention. First image 700A in FIG. 7A depicts the VTD in three dimensional perspective with semi-transparent rendering of the body to allow the scaffold disposed within to be evident. Second image 700B in FIG. 7A depicts a three-dimensional perspective view of the VTD comprising a cup body 7050, a resilient scaffold 7100, a handle 790 and a stem 780 connecting the cup body 7050 to the handle 790. Third to fifth images 700E to 700C respectively depict plan view, end elevation view towards the handle 790, and cross-sectional side elevation X-X respectively. Accordingly, the resilient scaffold 7100 within the cup body 7050 is evident in each together with the stem 780 and handle 790. The cup body 7050 may be flexible and formed from one or more materials having low Young's modulus such that it deforms relatively easily whereas the resilient scaffold 7100 is formed from a material having a higher Young's modulus. As depicted the resilient scaffold 7100 has a smooth upper surface towards the recess within the VTD whilst the lower portion consists of a series of rib elements tapering from maximum thickness at the end within the stem to minimum thickness at the distal end.

Figure 7C:
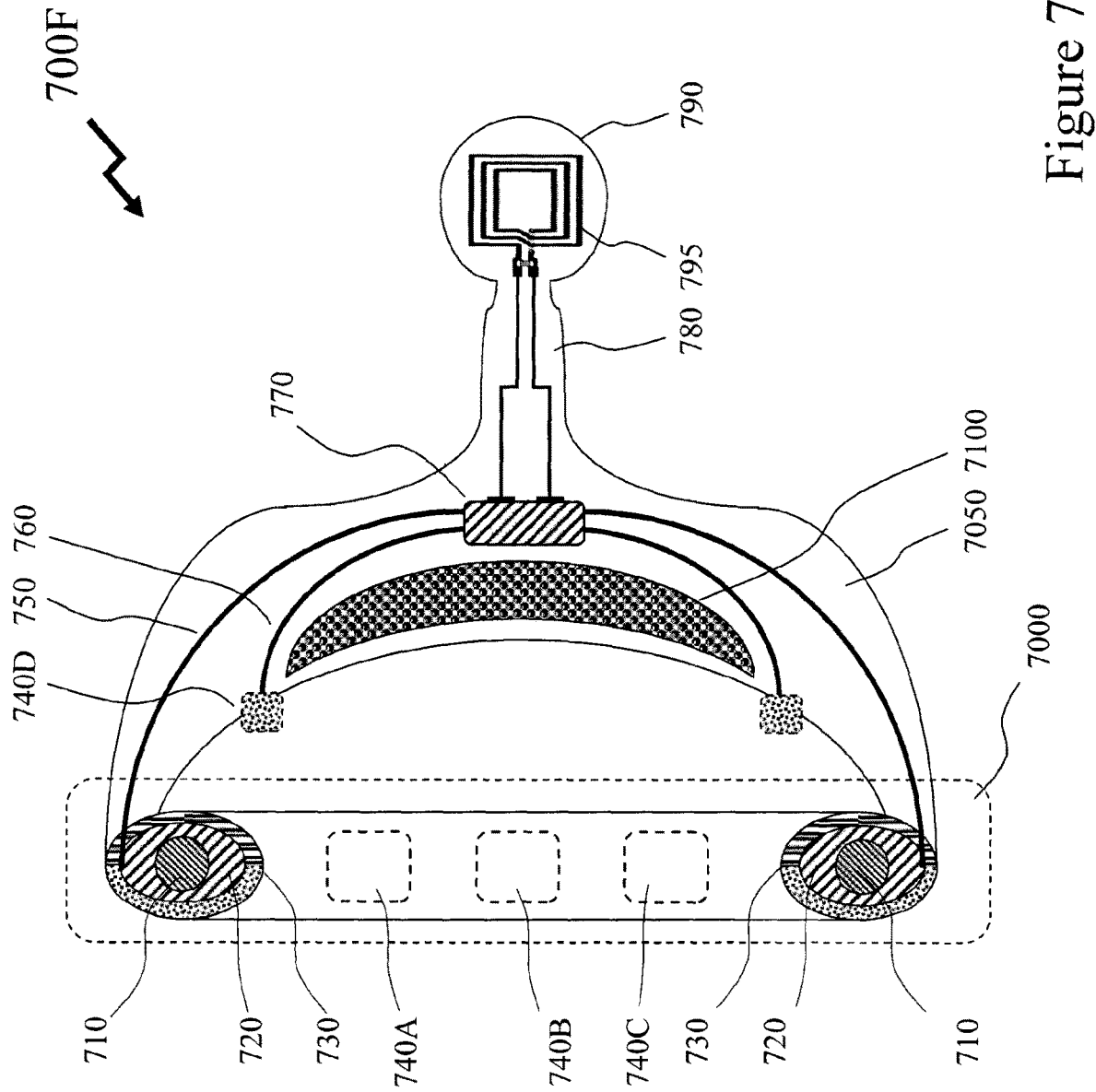

Referring to FIG. 7C there is depicted a VTD 700F according to an embodiment of the invention wherein the VTD 700F as depicted comprises many common elements to the VTD depicted in first to fifth images 700A to 700E in FIGS. 7A and 7B respectively. Accordingly, as depicted the VTD 700F comprises a cup body 7050, a ring portion 7000 of the cup body 7050 and handle 790 connected to the cup body 7050 via stem 780.

In contrast to the VTD depicted in first to fifth images 700A to 700E respectively in FIGS. 7A and 7B which is a passive VTD the VTD 700F is an active VTD. Disposed on the inner surface of the cup body 7050 are sensor element 740D which are coupled to an electronic circuit 770 which is itself coupled to an antenna 795 within the handle 790. The electronic circuit 770 may comprise a wireless circuit (not depicted for clarity), battery (not depicted for clarity), control electronics (not depicted for clarity), and memory (not depicted for clarity). The electronic circuit 770 is depicted within a thicker base region of the VTD 700F rather than the thinner walls of the cup body 7050. However, exploiting thin film flexible substrates etc. the electronic circuit 770 may be distributed within the cup body 7050 and/or ring portion 7000.

Accordingly, the cup body 7050 and handle 790 may be formed from elastic/rubber/flexible materials such as a medical grade silicone, for example, or others as described elsewhere within this specification. The sensor elements 740D provides measurements to the electronic circuit 770 with respect to, for example, whether there is fluid within the cup body 7050 which is either processed by the electronic circuit 770 to a small degree, such as averaging, filtering, etc. or to a heavier degree such as volume calculation, etc. The output of the electronic circuit 770 is coupled to an external device, e.g. a PED, via the antenna 795.

The ring portion 7000 of the VTD 700F comprises a structure such as depicted in FIG. 5A, for example, wherein it comprises a Scaffold 710, Shell 720, and Casing 730. Disposed around the ring 7000 are multiple sensors, depicted as sensors 740A, 740B, and 740C respectively. These are coupled to the electronic circuit 770 via electrical leads 750 within the cup body 7050. Accordingly, cup body 7050 may within embodiments of the invention provide a menstrual cup whilst ring 7000 provides a pessary function. Alternatively, the cup body 7050 may be perforated or formed from sections such that it will not retain fluid but the sensor elements 740D will detect the presence of fluid only rather than any level detection etc. which may be undertaken for example by providing multiple sensors disposed along the inner surface of the cup body 7050. Accordingly, the user may wear the VTD 700F during their normal activities and remove/clean/replace during their menstrual cycle.

Figure 8A:
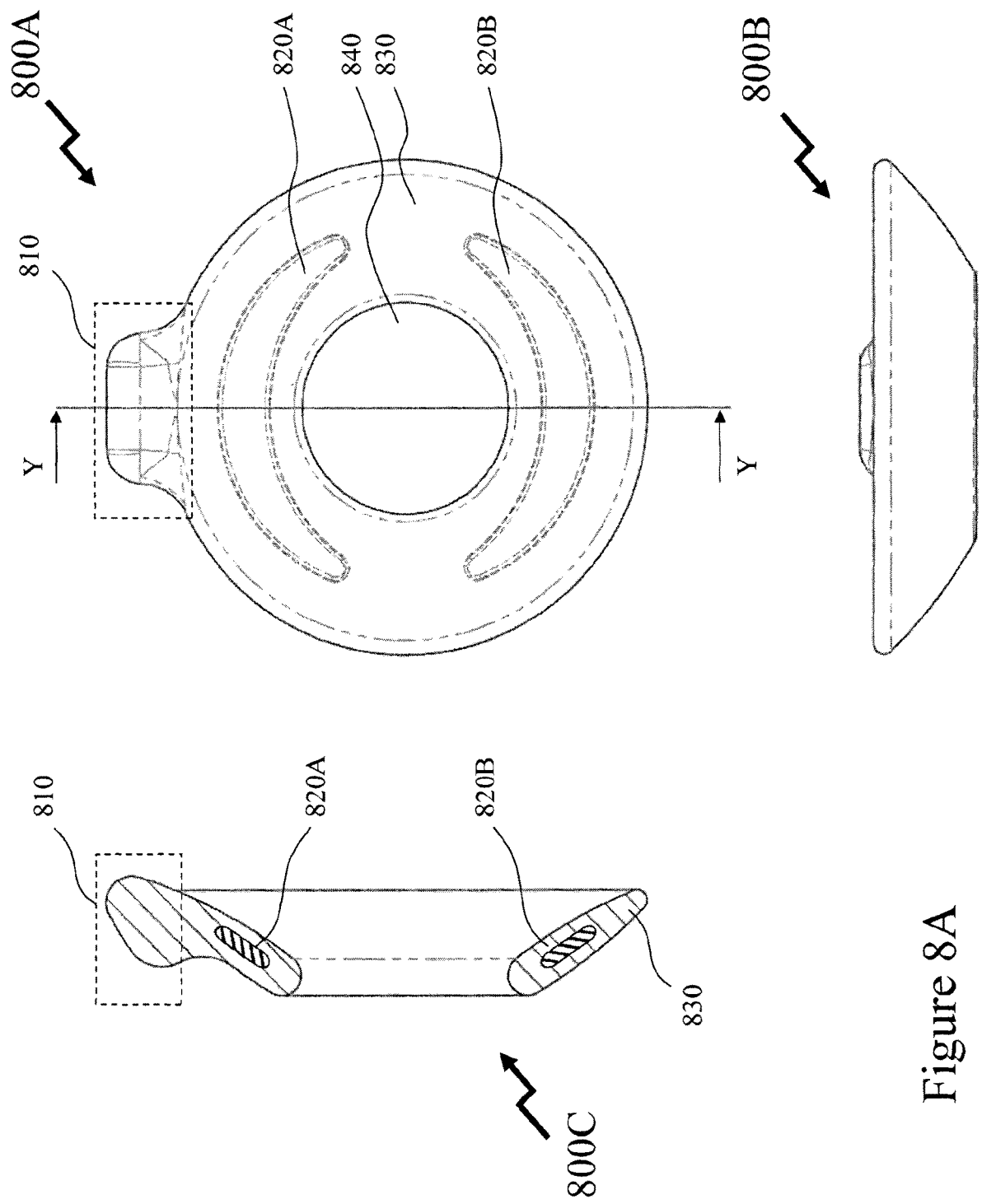
FIGS. 8A and 8B depict an exemplary USTD according to an embodiment of the invention.
Figure 8B:
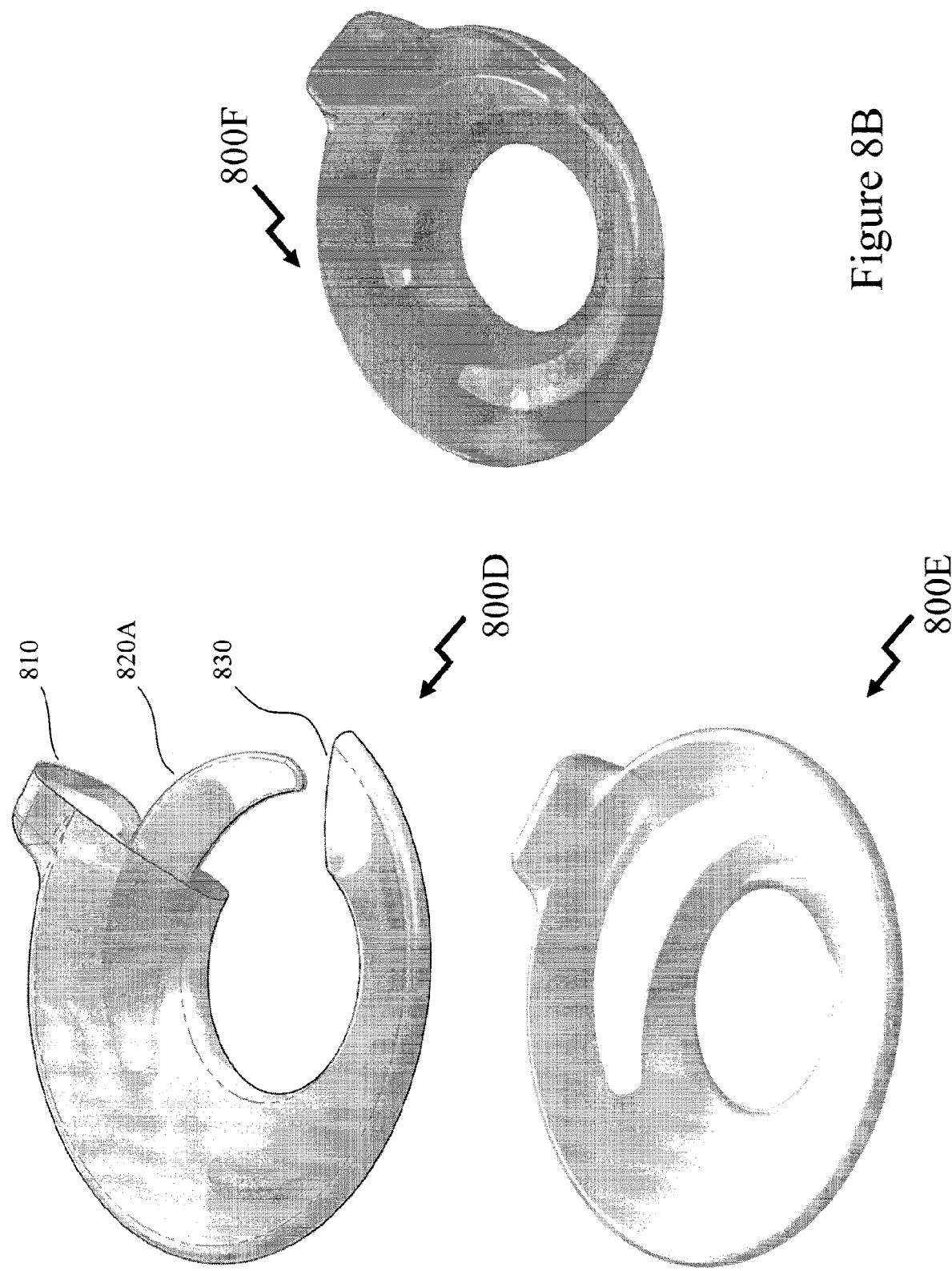

Now referring to FIGS. 8A and 8B there are depicted views of an alternate VTD according to an embodiment of the invention. Referring to FIG. 8A there are depicted first to third views 800C to 800A depicting plan view, end elevation view from the end away from knob 810, and cross-sectional side elevation Y-Y respectively. Accordingly, as depicted the VTD comprises a body 830 with a knob 810 disposed at one point around the periphery. Disposed within the body 830 are first and second resilient members 820A and 820B respectively either side of an opening 840. Whilst the first and second resilient members 820A and 820B respectively are depicted along a common axis with that of the knob 810 it would be evident that the first and second resilient members 820A and 820B may be disposed either side of the opening 840 along an axis that does not align with the knob 810. This VTD is then depicted in fourth to sixth images 800D to 800F respectively wherein:

Fourth image 800D is a three-dimensional model of the VTD with a portion of the body 830 and knob 810 removed to depict the first resilient member 820A within;

Fifth image 800E is a three-dimensional model of the VTD; and

Sixth image 800F is a three-dimensional image of an as fabricated VTD according to the embodiment of the invention depicted in first to fifth images 800A to 800E respectively.

Figure 9:
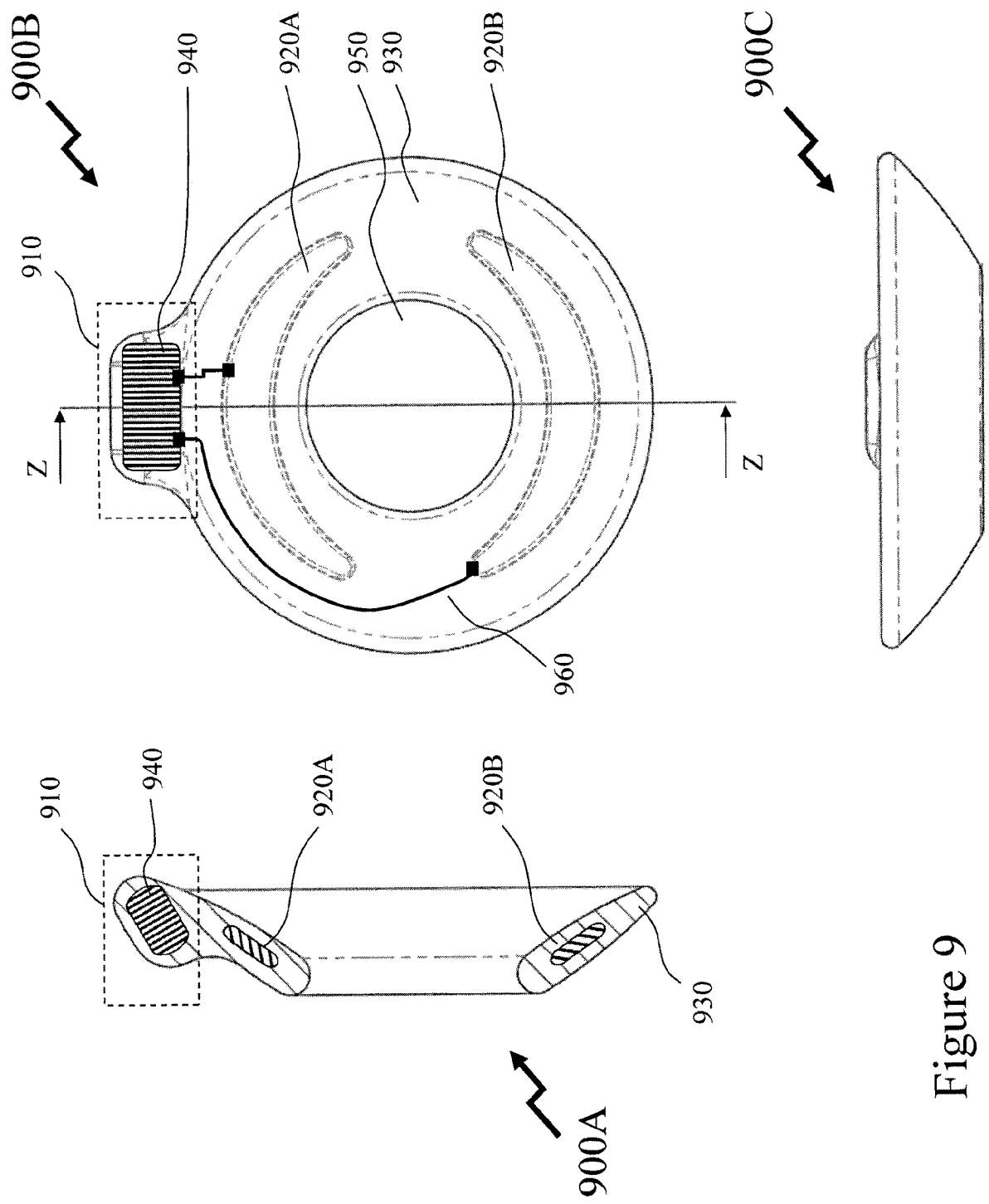
FIG. 9 depicts an exemplary USTD according to an embodiment of the invention.

Referring to FIG. 9 there are depicted first to third views 900C to 900A depicting plan view, end elevation view from the end away from knob 910, and cross-sectional side elevation Z-Z respectively. Accordingly, as depicted the VTD comprises a body 930 with a knob 910 disposed at one point around the periphery. Disposed within the body 930 are first and second resilient members 920A and 920B which are disposed either side of opening 950. Each of the first and second resilient members 920A and 920B is coupled to an electronic circuit 940 via an electrical connection 960. Accordingly, sensors (not depicted for clarity) forming parts of the first and second resilient members 920A and 920B respectively may provide measurements to the electronic circuit 940 and subsequently to another electronic device via an interface, e.g. a wireless interface (not shown for clarity) either forming part of the VTD or attached to the electronic circuit 740 within the VTD. Accordingly, the wireless interface may support wireless communications via a protocol/technique such as Bluetooth, Zigbee, etc. when employed in-situ or alternatively via a protocol/technique such as near field communications (NFC), radio frequency identification (RFID) when the VTD is external to the user or removed. Alternatively, within other embodiments of the invention the wireless communications interface may be employ a visible optical communications technique, an infra-red communications technique, an acoustic/ultrasonic communications technique, or if appropriate protection/sealing can be established a connectorized electrical interface such as electrical contacts, electrical connector etc.

Whilst within the VTDs depicted in FIGS. 8A, 8B and 9 the pair of resilient members are shown as having the same geometry and cross-section it would be evident from the description supra in respect of FIGS. 2 to 7C in respect of measuring, characterizing, modelling and manufacturing the VTD to the patient that the result may be an asymmetry of the VTD geometrically overall as well as in respect of the mechanical properties and dimensions of the first and second resilient members 920A and 920B respectively. Within other embodiments of the invention one of the first and second resilient members 920A and 920B may be omitted if that achieves the overall objective of the VTD for that patient. Alternatively, the width, thickness, angular range (effectively length of the insert) may be varied of one and/or both resilient members. Similarly, the number of resilient members may be 1, 2, 3, 4, 5, or more. Optionally a resilient member may comprise multiple resilient elements linked by one or more joining members that provide for a different resiliency along their axis relative to the axis of the resilient elements. As depicted the body 830 in FIGS. 8A and 8B together with the body 930 in FIG. 9 may be viewed as a frustum of a hollow conical design, i.e. a section defined of a hollow conical element defined by a pair of parallel planes. Alternatively, it may be viewed as a frustum of a conical design which has then had its central region removed to provide openings at either end.

Figure 10:
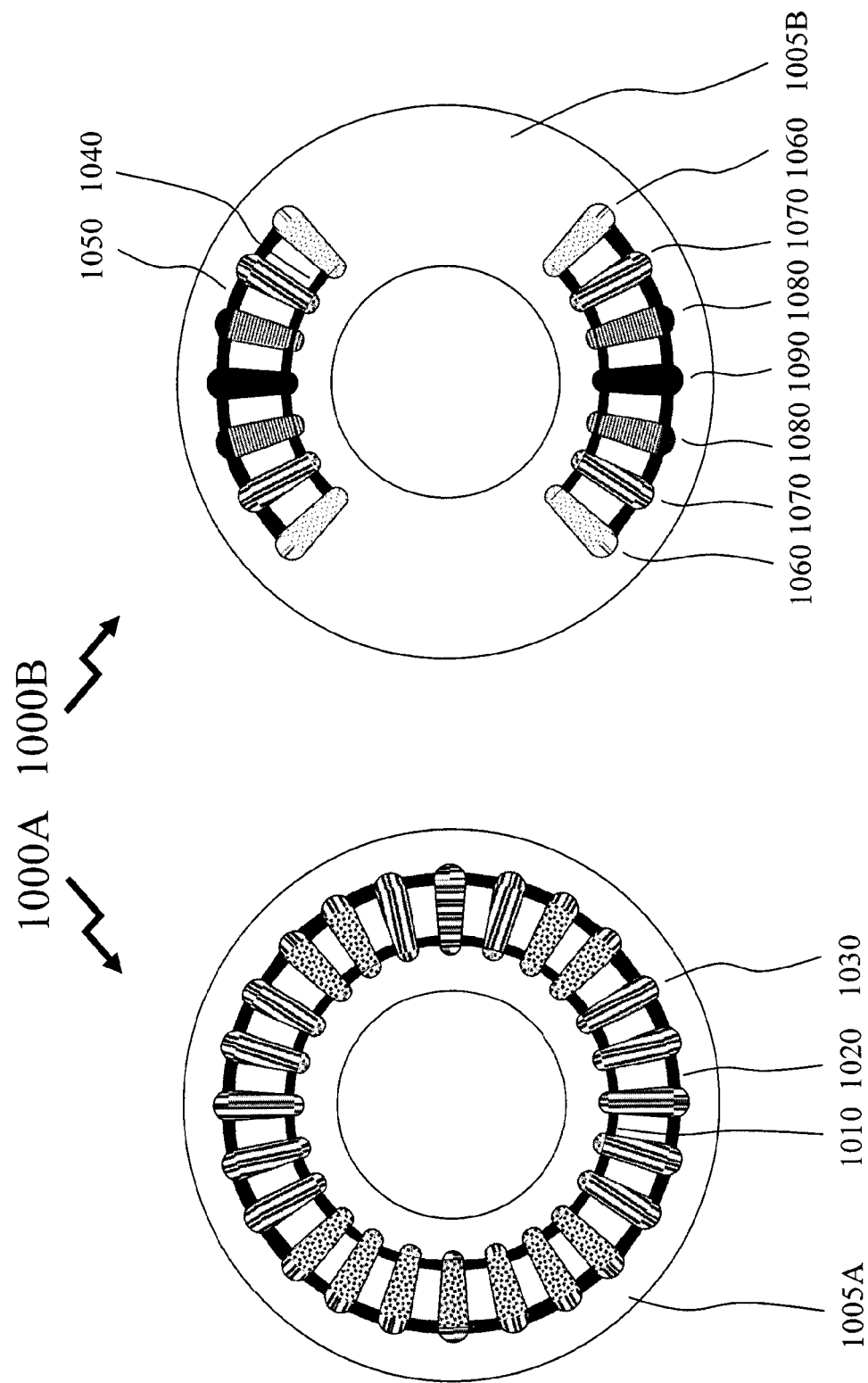
FIG. 10 depicts exemplary USTDs according to embodiments of the invention.

Examples of such VTD configurations being depicted in FIG. 10 with first and second images 1000A and 1000B respectively. Within first image 1000A the VTD comprises a body 1005A within which are a plurality of resilient elements 1030 which are coupled via first and second joining rings 1010 and 1020 respectively. For example, the plurality of resilient elements 1030 may be of low flexural modulus (e.g. rigid) whilst the first and second joining rings 1010 and 1020 have high flexural modulus (e.g. flexible). Alternatively, in second image 1000B the VTD comprises a body 1005B within which are a pair of coupling rings 1040 and 1050 that link a set of resilient elements having first to fourth designs 1060, 1070, 1080, and 1090 respectively each of which presents a differing degree of resiliency.

Whilst the embodiments of the invention have been described and depicted in respect of a scaffold, shell and casing it would be evident that alternate designs may employ solely scaffold-casing, shell-casing Optionally, VTDs according to embodiments of the invention as described and depicted in respect of FIGS. 5A-5C to 10 may be coated in addition to the outer casing with one or more pharmaceutical compounds according to the performance goals of the VTD with respect to one or more of antimicrobial protection, contraception, and drug delivery. Optionally, the VTD may be intended for use over a period of say 3 months, 6 months, a year prior to being replaced wherein absent any additional data/information to the contrary a replacement VTD may be provided based upon the stored Computer Aided Design (CAD)/Computer Aided Manufacturing (CAM) files for the user.

Accordingly, the processes and devices described and depicted within FIGS. 2 and 5A to 10 respectively relate to a VTD although as evident from the discussions below in respect of FIG. 11 they may relate to a USTD of which a VTD is a specific embodiment Accordingly, a patient complains of a condition or symptom such as urinary or fecal incontinence or is at risk of a condition or symptom such as symptomatic POP, urinary or fecal incontinence, pre-term birth etc. Accordingly, measurements are made with respect to the patient (user) for example with respect to a VTD this may include a form of vaginal distention such as through one or more of vaginal tactile imaging, vaginal manometry, balloon distension, placement of pessary or intravaginal device inside of vaginal balloon to perform distention, etc. together with one or more forms of imaging.

Based upon the measurements made a model is created for the VTD or USTD. Within the following description and discussion including reference to Tables 2 to 4 the device is a pessary although it would be evident that other devices may be modelled, simulated, and manufactured for a user. According to embodiments of the invention and as noted above a device may be formed from a scaffold only, a scaffold with a casing, a scaffold with a shell, a scaffold with a shell and casing, a shell with a casing, a shell, and a casing. Each element such as a scaffold, casing, and shell may be a single material or it may be formed from two or more materials. Optionally, the two or more materials are disposed at different positions of the VTD or USTD in order to provide different mechanical properties to the VTD or USTD at that positions as defined relative to the user's physiology.

Based upon assessment of the model then the device is manufactured and provided to the user. Optionally, the measurements and/or assessments performed with respect to the user are adjusted, defined or specified in dependence upon a "level" of the product. For example, three levels of product and user assessment are considered within this specification although it would be evident that there may be only one level, two levels, or three or more levels. Accordingly, considering three levels then for a "Level 1 Product" the user assessment may comprise vaginal manometry and the device a ring shaped pessary established in dependence upon 3 or 4 variables for example within the parametric model. Such a pessary being depicted for example by FIGS. 8A and 8B respectively. A "Level 2 Product" may be established in dependence upon vaginal manometry in conjunction with three-dimensional (3D) imaging and either a parametric model or generative design. A "Level 3 Product" may be established in dependence upon vaginal manometry, 3D imaging and QoL data and/or feedback whilst a generative design or AI-assisted parametric modelling are employed to generate the design.

Referring to Table 2 parameters of the user are listed together with pathological indications and vaginometry correlation whilst Tables 3 and 4 list measurement examples using vaginal manometry discretely or in combination with 3D imaging together with their associated indicated pessary design parameters.

TABLE 2

Exemplary User Vagina Parameters with Pathological Indications

| POP-Q | Indication of Pathology | Vaginometry Correlation |
|---|---|---|
| Ba | Degree of anterior POP | Anterior Wall Shape |
| Bp | Degree of posterior POP | Posterior Wall Shape |
| C/D | Degree of apical POP | Distal Wall Shape |
| gH | Risk of falling out | Levator Hiatus |
| Tvl | Degree of longitudinal space filling necessary | Vaginal Length |

TABLE 3

Exemplary Vaginal Manometry Measurements with Pessary Design Indications

| Vaginal Manometry | Indication of Pessary Design Parameter | Notes |
|---|---|---|
| Vaginal capacity | Degree of space filling necessary | 1 |
| Vaginal length | Degree of longitudinal space filling necessary | 2 |
| Vaginal capacity + length (calculated) | Pessary sizing, volume, OD $V = \pi \cdot r^2 \cdot h \quad V = \frac{4}{3} r^3$ | 3 |
| Urethral or Rectal Closure Volume | Size required to stop urinary or faecal prolapse | |

Notes:
1. Volume at pressures near Pabd.
2. Length "P" line to C or cuff at pressures near Pabd.
3. Simple combinations of cylindrical/spherical models may be used to estimate maximal vaginal width (for space filling) without need for actual 3D US reconstruction.

TABLE 4

Exemplary Vaginal Manometry and 3D Imaging Measurements with Pessary Design Indications

| Vaginal Manometry with 3D Imaging | Indications for Pessary Design Parameters | Notes |
|---|---|---|
| Vaginal Shape at various distended volumes (anterior, posterior, side, and distal wall) | Pessary Shape (x, y, z plane), likelihood of expulsion and design compensation for it | 4 |
| Levator hiatus (LH) | Pessary diameter (OD, ID), scaffold shape and rigidity | 5 |
| Levator avulsion (yes/no) | Pessary OD/ID, scaffold shape and rigidity | 6 |
| PF strength (PFS = Pvag – Pabd during contraction and push) | Pessary OD/ID, scaffold shape and rigidity | 7 |
| Vaginal extensibility | A measure of how aggressive sizing can be as reduced extensibility can yield higher risk of ulceration/erosion with wider pessary. May weight designs to employ smaller values | 8 |
| Vaginal stiffness | May be incorporated as an additional factor for determining aggressiveness on sizing or softness of shell and/or part of pessary | 9 |

TABLE 4-continued

Exemplary Vaginal Manometry and 3D Imaging Measurements with Pessary Design Indications

| Vaginal Manometry with 3D Imaging | Indications for Pessary Design Parameters | Notes |
| --- | --- | --- |
| Stress-relaxation parameters | May provide indicator for degree the tissue will "loosen" up after the pessary is inserted for "long" period of time. For example, more relaxation may mean we can be more aggressive on sizing as the tissue will eventually relax | |
| Vaginal wall thickness | Thinner wall and/or softer shell | 10 |

Notes
4: May be too many dimensions and/or parameters for some parametric model designs but could be an optimal measure or image for generative design.
5. Diameter may be used to determine pessary width such that the levator plate may be used to block the pessary from falling out.
6. If major avulsion, then less reliance on levator hiatus for preventing fall out.
7. Another indicator of the degree to which pessary design can rely on levator hiatus to prevent fallout.
8. Calculated as the X intercept of linear region. This property indicates how much a tissue may be stretched before significant stress is built up within its walls.
9. Calculated as slope of linear region.
10. May reduce risk by reducing the boundary condition effect on mucosa causing tissue erosion.

Within the preceding descriptions and depictions with respect to embodiments of the invention the methodologies of measurement, analysis and manufacturing of a custom device for a patient have been with respect to a vaginal therapy device (VTD). However, embodiments of the invention with respect to measurement, analysis and manufacturing of a custom device for a patient may be undertaken with respect to other devices including therapeutic devices and non-therapeutic devices. The inventors refer to these as User Specific Therapeutic Devices (USTDs). Such devices may include, but are not limited to:

Vaginal therapeutic devices with antimicrobial properties;
Vaginal dilators;
Sexual stimulation devices such as dildos, vibrators, artificial vaginas etc.;
Birth control devices such as cervical caps, diaphragms, contraception delivery, etc.;
Menstruation devices such as menstrual cups;
Prosthesis such as penile extensions, cervical constructs, etc.;
Infection prevention devices such as intravaginal ring (IVR) for pre-exposure prophylaxis regimens, etc.;
Orthotics such as prophylactic braces, functional braces, rehabilitation braces etc. including, but not limited to, lower limb orthotics for foot, knee, ankle, ulcer, etc. or upper limb orthotics for elbow, wrist, forearm, hand, finger, thumb etc.;
Orthodontics such as braces, retainers, extenders, etc.; and
Sleep therapy devices for nasal and/or oral orifice maintenance, etc.

Optionally, within embodiments of the invention a USTD according to an embodiment of the invention may replace, interact with, facilitate the use of, restore the function or, and/or strengthen body system(s), body region(s) and/or body part(s) of a subject including, but not limited to the head, mouth, neck, forehead, jaw, cheek, chin, upper limb, finger, thumb, hand, wrist, forearm, elbow, arm, shoulder, thorax, chest, rib cage, abdomen, groin, back, spine, spine components, vertebrae, sacrum, coccyx, intervertebral disks, pelvis, perineum, lower limb, hip, buttocks, thigh, knee, leg, calf, ankle, foot, toes, musculoskeletal system, bones, cartilage, ligaments, tendons, circulatory system, digestive system, endocrine system, integumentary system (e.g. skin, hair, nails, etc.), lymphatic system, reproductive system, respiratory system, and urinary system.

Figure 11:
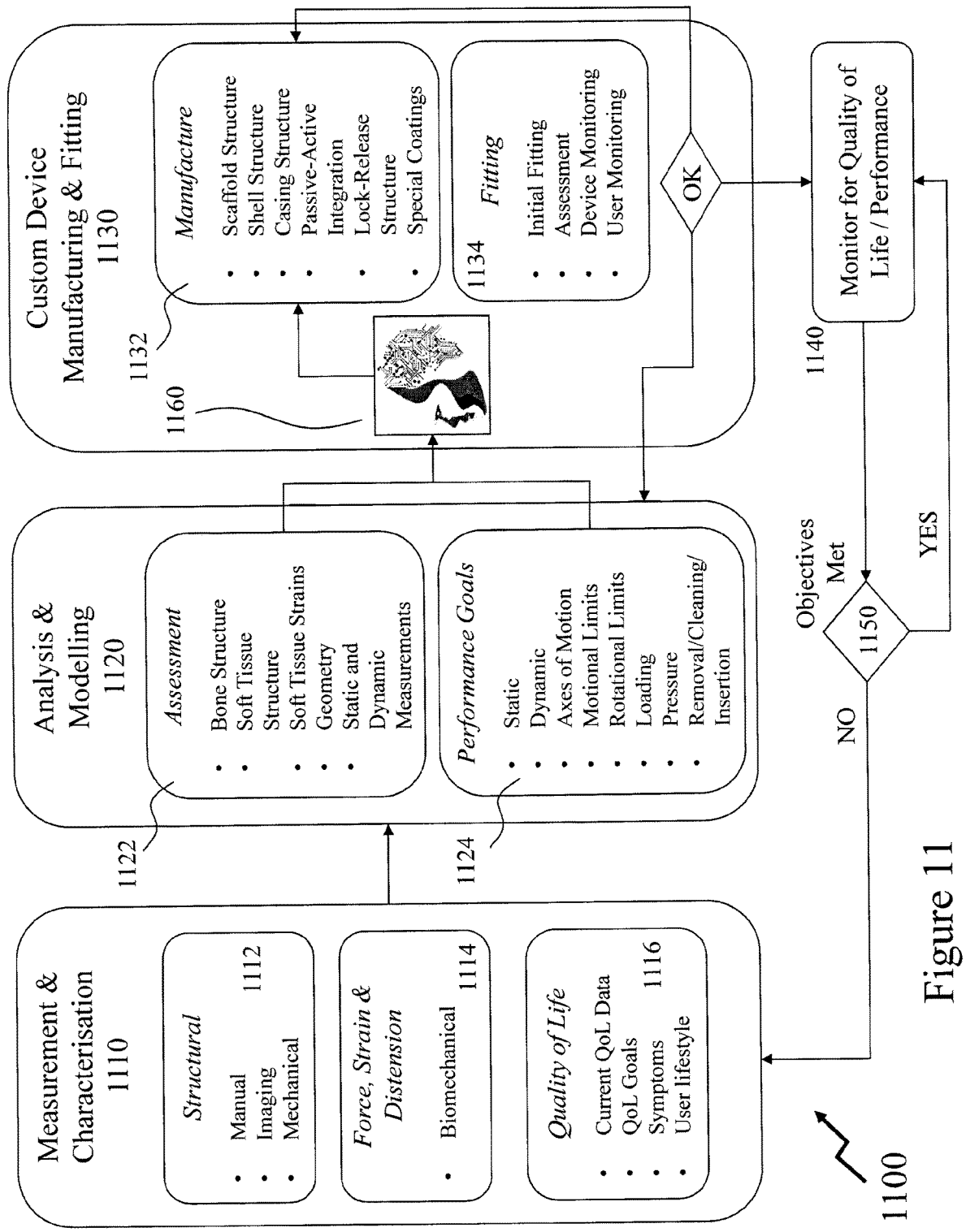
FIG. 11 depicts an exemplary process flow for providing a user with a custom therapeutic device according to an embodiment of the invention.

Accordingly, referring to FIG. 11 there is depicted an exemplary process flow 1100 for providing a user with a user specific therapeutic device (USTD) according to an embodiment of the invention such that the process is reduced from a bewildering array of USTD types and dimensions to a single USTD option without significant effort from either the patient or the clinician. Accordingly, at step 1110 the process begins with the step of Measurement and Characterisation (M&C) 1110 before progressing to Analysis and Modelling (A&M) 1120 and Custom Device Manufacturing and Fitting (CUDEMAF) 1130 wherein the patient (user) is now provided and fitted with a custom USTD. Next, the process proceeds to step 1140 wherein ongoing monitoring of quality of life (QoL) and performance of the USTD wherein a decision process 1150 may determine whether the objectives of the USTD are being met or still being met on an ongoing basis and hence determine whether monitoring should continue or whether the process should begin again with step 1110. An ongoing monitoring and cyclic process may be appropriate for a variety of USTD use cases including, but not limited to, changing physical characteristics of the user, changing physiology of the user, and degradation of the USTD. Accordingly, as depicted M&C 1110 comprises three sub-processes, these being, Structural 1112, Force, Strain and Distension 1114, and Quality of Life 1116.

Within embodiments of the invention the custom USTD may be employed in combination with other therapies and/or pharmaceutical coatings etc. in order to combine a custom USTD with regenerative medicine. Accordingly, within other embodiments of the invention a USTD according to an embodiment of the invention may exploit an energy delivery system such as infrared irradiation or ultraviolet irradiation for example. A custom USTD may also be employed in conjunction with other medical procedures and/or treatment regimens including, for example, exploitation of stem cells.

Structural 1112 may comprise one or more measurements of the user's anatomy and/or measurements of the user's physical characteristics such that one or more characteristics such as the dimensions of the user's major anatomical structures, anatomical geometry, etc. are defined. Such measurements may exploit one or more techniques including, mechanical measurements, ultrasound imaging, magnetic resonance imaging (MRI), elastography, acoustic analysis, tactile imaging, photoacoustic (optoacoustic) imaging, tomography, echocardiography, functional near-infrared spectroscopy, electrical impedance tomography, and light detection and ranging (LIDAR). Alternatively, mechanical based devices may be employed to perform measurements and/or support one or more transducers for one or more imaging techniques, manual processes etc.

Force, Strain and Distension 1114 may comprise one or more measurements of characteristics of the user's anatomy and/or measurements of the user's physical characteristics such as compliance/resilience of the user's tissues, the movement(s) and strength of user's musculature within the appropriate anatomical regions. These may involve mechanical and/or imaging testing discretely or in combination with other tests. Such tests may include, but not be limited to:

"Pressure" test to determine force applied as user performs an action, e.g. chew, close mouth, stand up, walk, step up a step, etc. wherein such measurements may be on a single longitudinal axis, multiple longitudinal axes, single rotational axis, multiple rotational axes; or a combination of longitudinal and rotational axes;

Tactile imaging for force and strain measurements;

Elastography from ultrasound as well as other measurements.

Techniques may include those identified supra and others including, but not be limited, leak point pressure, vaginal LIDAR, vaginal manometry, ultrasound, elastography, strain sensor array, acoustic analysis, tactile imaging, and photoacoustic (optoacoustic) imaging. The measurements performed within Structural 1112 and Force, Strain and Distension 1114 may be statically acquired, i.e. with the user sitting/laying/standing within a clinic or another environment and/or dynamically acquired with the user performing one or more routine aspects of their life such as walking, exercising, running, lifting, bending, etc.

In contrast to the Structural 1112 and Force, Strain and Distension 1114 the Quality of Life 1116 is an assessment. Accordingly, Quality of Life (QoL) 1116 may include, but not limited to, current QoL data for the user (patient), QoL goals for the user (patient), symptoms experienced by the user, and user lifestyle.

Accordingly, QoL 1116 establishes baseline QoL data which may be employed subsequently for the monitoring, QoL and performance of the USTD once manufactured and employed according to embodiments of the invention. Accordingly, for one user a QoL goal may be the elimination of a symptom that occurs only during sexual activity whilst for another it may during a specific exercise, sporting activity, etc. or for another over specific periods of time and/or generally monitored etc. Additionally, the USTD in terms of being permanent, semi-permanent, or temporary is established wherein for temporary use at least the installation/removal means and/or mechanisms are established with the user. For permanent and semi-permanent the installation/removal means are geared primarily to the clinician rather than the user.

In establishing the QoL 1116 a user may employ an application upon a PED and/or FED in order to track the user's (patient's) perceived QoL, to monitor and/or log even occurrences such incontinence, pain, prolapse, pessary fall out, etc. From M&C 1110 the process proceeds to A&M 1120 wherein sub-processes of Assessment 1122 and Performance Goals 1124 are undertaken. Within Assessment 1122 the data obtained within the M&C 1110 step are analysed, for example, through their entry into a human body (anatomical) model (HBM) of the appropriate body region or body regions to define a series of two-dimensional (2D) and/or three-dimensional (3D) perspectives of the user's anatomy as well as other parameters.

Within Performance Goals 1124 the QoL 1116 data is established as specific static and dynamic performance goals for the USTD, axes of motion, motional limits, rotational limits, loading, pressure etc. These aspects may include, but are not limited to, whether the USTD is to address long term or short term issues, whether the USTD is to address recurring episodes together with frequency etc., degree of comfort level required, will or can the user perform self-removal/cleaning/insertion etc., will this require periodic visits to a physician or clinic, and will any coatings require the user periodically dispose of the USTD and use a new USTD. Additionally, additional characteristics may be established with respect to providing an antimicrobial coating, providing controlled pharmaceutical product release(s) such as proteins, regenerative medicine(s), pain killers, or other drugs for the user. These together with the data from Assessment 1122 are employed in defining the custom USTD for the user in terms of physical geometry, e.g. dimensions of any ring structure, knob, support etc. Additionally, the mechanical properties of the custom USTD are defined in respect of the flexibility, dimensional stability, installation/removal means, physical characteristics of the USTD such as smooth/contoured surfaces and/or regions, etc. as well as other aspects such as any locking and/or release mechanisms.

Based upon the established mechanical and physical requirements together with appropriate aspect of the QoL requirements the process in Custom Device Manufacturing and Fitting (CUDEMAF) 1130 proceeds with a sequence comprising Manufacture 1132 and Fitting 1134. The accumulated data from the Analysis & Modelling 1120 as defined within Assessment 1122 and Performance Goals 1124 is coupled to an Artificial Intelligence (AI) Engine 1160 which employs a plurality of algorithms which may exploit one or more approaches including, but not limited to, those based on symbol manipulation, cognitive simulation, logic-based programming, anti-logic programming, natural language processing, knowledge based, sub-symbolic, embodied intelligence, computational intelligence and soft computing, and statistical either individually or in combination such as within methodologies such as the intelligent agent, multiple interacting agents in a multi-agent system, and a hybrid intelligent system.

Within Manufacture 1132 the custom USTD is defined in respect of the materials providing its physical geometry with the desired mechanical properties as well as external characteristics. Accordingly, the custom USTD may be defined by one or more aspects including, but not limited to:

Scaffold structure by dimension(s), material(s) etc.

Shell structure by dimension(s), material(s) etc.

Casing structure by dimension(s), property or properties, material(s).

Passive-active integration such as is USTD passive or does it embed sensor(s), control and/or data logging circuitry, wireless interface(s) etc.

Lock-release structure.

Coatings.

Accordingly, a CAD model is established from which the Manufacture 1132 process is undertaken. Within an embodiment of the invention an initial CAD model may be established by combining three-dimensional (3D) modelling with computational fluid dynamics (CFD), finite element analysis (FEA), and/or multi-organ free-body diagram models. The CAD model may be simplified to reduce the required computational power and complexity of the processing applied prior to the AI Engine 1160 executes. The AI Engine 1160 may process based upon this initial pre-processing solely or may apply the pre-processing to a more complete human body (anatomical) model and USTD model in order to define the USTD design, CAD, and materials requirements. Optionally, the pre-processing may be bypassed where appropriate levels of computing resources are available. Accordingly, a USTD as designed and manufactured may range from a passive USTD through to an active USTD, with lock-release structure, anti-microbial coating, and wireless interface for transmitting data logging data relating to the user.

Optionally, within embodiments of the invention the USTD may in addition to sensors include actuators that apply pressure to predetermined regions of the user or may support the user's body motion. Optionally, the USTD may provide controlled release of one or more pharmaceutical agents such as by opening a reservoir to expose said one or more pharmaceutical agents, employ microneedles to inject one or more pharmaceutical agents, etc.

Within Fitting 1134 the custom USTD is provided to the user and either fitted by themselves, e.g. for temporary use USTD that the user will insert/remove as desired, or by a clinician, e.g. semi-permanent or permanent use. At this point one or more assessments may be carried out such as outlined previously in respect of Structural 1112 and/or Force, Strain and Distension 1114 whereby mechanical, imaging, static and/or dynamic assessment etc. are performed to assess the USTD fit against the target design/user physiology etc. This stage may also include device monitoring, e.g. via internal sensors to the USTD, as well as user monitoring, e.g. by personally noting performance of the USTD etc. Based upon these results a determination is made as to whether the USTD meets the initial requirements wherein if the determination is positive then the process proceeds to step 1140. If not, then the process proceeds to loop back to either A&M 1120 or CUDEMAF 1130 according to the nature and/or complexity of the modifications/amendments required.

In step 1140 the user employs the USTD on an ongoing basis wherein device monitoring, e.g. via internal sensors to the USTD, as well as user monitoring, e.g. by personally noting performance of the USTD etc. are performed wherein periodically this data is employed in determining whether the objectives for the USTD were met in step 1150. If yes, then the process loops back to step 1140 otherwise it proceeds back to step 1110. For example, a young user may require multiple USTDs within the space of a few years/decade during their childhood, adolescence, puberty, etc. with evolving dimensions and requirements whereas an elderly user may require a single adjustment or no adjustment according to their circumstances.

Now referring to FIGS. 12A and 12B there are depicted first and second configurations 1200A and 1200B respectively for performing ultrasound measurements upon a user according to embodiments of the invention in order to obtain user specific measurement data for performing design and simulations for providing a USTD, or more specifically a VTD. Accordingly, in FIG. 12A with first image 1200A a simplified cross-section of a user's anatomy is provided identifying the user's bladder 1210, uterus 1220, vaginal wall 1250, anus 1260 and rectum 1270. Disposed within the user's vagina as defined by the vaginal wall 1250 and uterus 1260 a balloon 1290 filled with a fluid which has been pumped into the balloon 1290 via tubing 1280 from a fluidic system attached to the tubing 1280, e.g. a pump, reservoir, pressure sensor etc. Accordingly, the fluid is pumped into the balloon 1290 until a predetermined pressure is reached implying the balloon has filled the user's vagina. An ultrasound probe 1240A is then attached to the balloon 1290 so that the fluid within the balloon 1290 couples the ultrasonic pulses from the ultrasound probe 1290 to the user's vaginal walls etc. Within FIG. 12A the ultrasound probe 1240A is coupled to the balloon 1290 via a ring 1295A on the balloon 1290 so that the ultrasound probe 1240A and balloon 1290 are sealed together so that fluid is sealed within and contacts the ultrasonic transducer.

Referring to FIG. 12B there is depicted an alternate configuration in second image 1200B with a simplified cross-section of a user's anatomy is provided identifying the user's bladder 1210, uterus 1220, vaginal wall 1250, anus 1260 and rectum 1270. Disposed within the user's vagina as defined by the vaginal wall 1250 and uterus 1260 a balloon 1290 filled with a fluid which has been pumped into the balloon 1290 via tubing 1280 from a fluidic system attached to the tubing 1280, e.g. a pump, reservoir, pressure sensor etc. Attached to the end of the balloon 1290 is a ring 1295B through which an ultrasonic probe 1230 is disposed which is attached to probe body 1240B. Optionally, the ring 1295B is formed from an elastic material such that the ring 1295B collapses back around the body of the ultrasonic probe. Within other embodiments of the invention the ring 1295B may clamp the balloon to the ultrasonic probe. Accordingly, the ultrasonic probe 1230 transmits ultrasonic signals which are coupled to the user's body via the fluid within the balloon and reflected signals are then coupled back through the fluid to receivers within the ultrasonic probe 1230 and coupled to the probe body 1240B. Accordingly, ultrasonic probe 1230 allows for multiple ultrasound transducers to be deployed in predetermined arrangement.

Optionally, other sensors and/or transducers may be deployed within the ultrasonic probe 1230 (or ultrasound probe 1240A in first image 1200A in FIG. 12A). These may include, but not be limited to, temperature sensors, heater(s), cooler(s), optical emitter(s), optical detector(s), microwave/RF transducer(s), and electrical contacts. Within the embodiments of the invention the balloon 1290 is filled with a predetermined fluid compatible with the probe, e.g. transmitting ultrasound; transmitting ultrasound and low optical absorption at required wavelengths, transmitting ultrasound, low optical absorption at required wavelengths and thermally conductive, etc. The fluid may be pumped into the balloon until a predetermined threshold is reached, e.g. predetermined volume, predetermined pressure, predetermined back pressure etc. The tubing 1280 may be demountably coupled to the balloon 1290 allowing the balloon 1290 to be disposable and to ease use of the balloon for the user and/or clinician. Similarly, the balloon may be demountably attached to the ultrasonic probe 1230 and/or ultrasonic probe 1240A.

Figure 13:
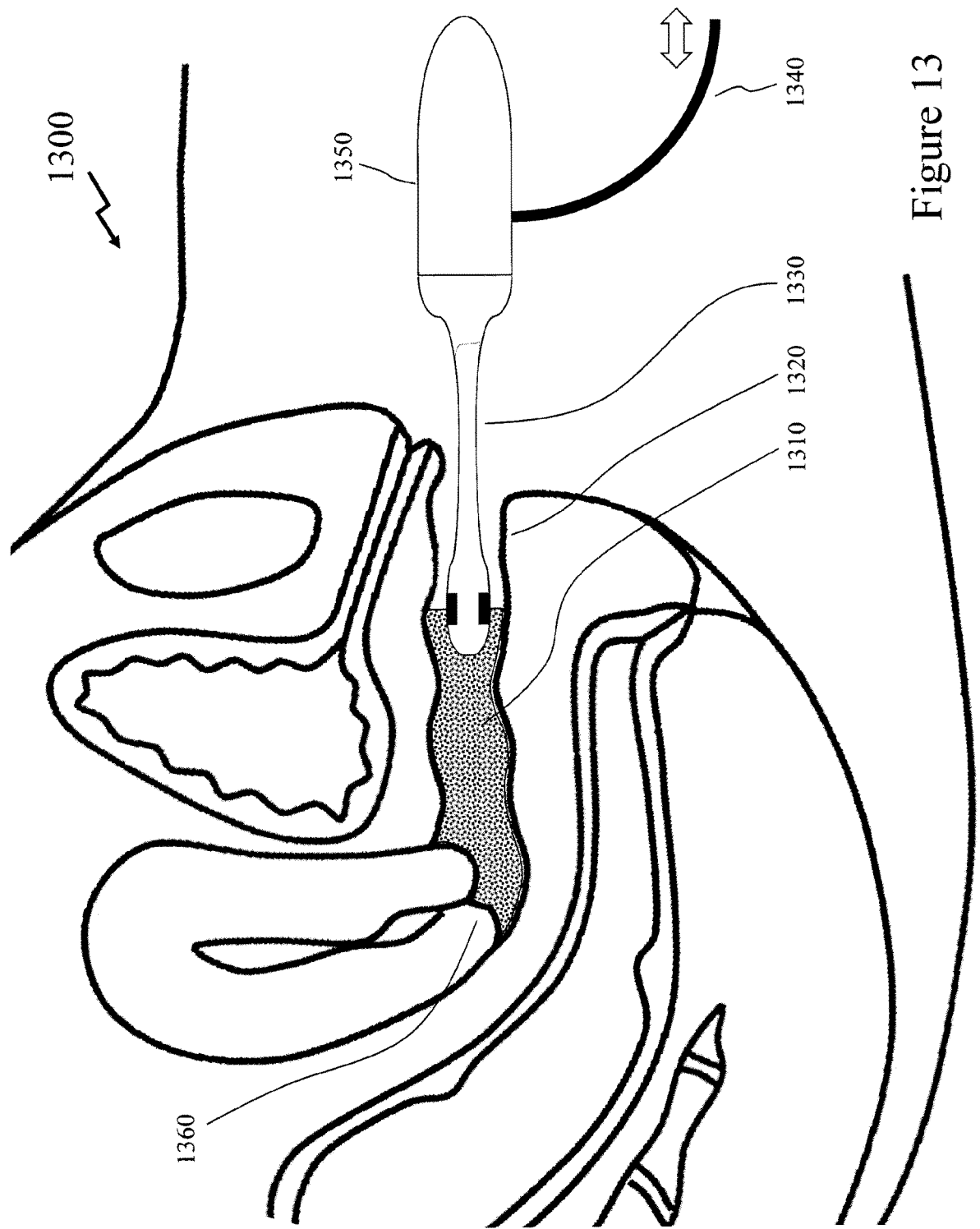
FIG. 13 depicts an exemplary configuration for performing assessment and/or measurements according to an embodiment of the invention.

Now referring to FIG. 13 there is depicted an exemplary configuration for performing assessment and/or assessments upon a user according to an embodiment of the invention in order to obtain user specific measurement data for performing design and simulations for providing a USTD, or more specifically a VTD. Accordingly, in FIG. 13 within image 1300 a simplified cross-section of a user's anatomy is provided in common with that in FIGS. 12A and 12B respectively where the vaginal wall 1320 and cervix 1360 are depicted. Accordingly, as depicted there is disposed within the user's vagina as defined by the vaginal wall 1320 and cervix 1360 a balloon 1310 filled with a fluid which has been pumped into the balloon 1310 from a probe connected via tubing 1340 to a fluidic system comprising, for example, a pump, a reservoir, a pressure sensor etc. Accordingly, the fluid is pumped into the balloon 1310 until a predetermined pressure is reached implying the balloon 1310 has filled the user's vagina. The probe is depicted as comprising a body portion 1350 and insertable portion 1330. The balloon 1310 being attached to the insertable portion 1330, as depicted at the end of the insertable portion 1330 although within other embodiments of the invention the balloon 1310 may be attached at a different position on the insertable portion 1330. Within some embodiments of the invention the probe, comprising insertable portion 1330 and body portion 1350, is passive whereas within other embodiments of the invention the probe contains one or more transducers. For example, the probe may contain an ultrasonic transducer for generating and receiving ultrasonic signals whereas within other embodiments of the invention the probe may contain an ultrasonic transducer to receive ultrasonic signals generated by an ultrasonic transducer external to the user which is moved relative to the user. Alternatively, the probe may contain temperature sensor(s), electrical contacts, control and measurement circuit(s), heater(s) etc. As depicted the probe 1240 is attached to the balloon 1310 so that the fluid within the balloon 1310 is retained within the balloon. Within other embodiments of the invention the fluid may have a high viscosity so that a high quality seal is not required. Optionally, the body portion 1350 and insertable portion 1330 of the probe may have a similar external geometry rather than the larger body portion 1350 relative to the insertable portion 1330 within FIG. 13. Within embodiments of the invention the insertable portion 1330 may be disposable whereas in other embodiments of the invention the insertable portion 1330 and body portion 1350 may be disposable.

Referring to FIGS. 12A, 12B and 13 placement of a balloon and its use in association with a probe have been described as providing measurements and/or assessments. Within other embodiments of the invention the balloon and/or probe may be employed in conjunction with a pessary or intravaginal device deployed within or as part of the vaginal balloon. Whilst the embodiments of the invention have been described and depicted in respect of a VTD and a balloon deployed vaginally it would be evident that embodiments of the invention may also be employed for urethral or anal deployment for example. A pessary or intravaginal device may provide for distension of one or more regions of the user's vagina or cervix, for example.

Within the embodiments of the invention described and depicted supra in respect of FIGS. 1 to 13 the design process has been described and depicted as exploiting an Artificial Intelligence (AI) Engine which converts data from analysis and/or modelling activities, e.g. stage Analysis and Modelling 220 in FIG. 2 for a VTD or Analysis and Modelling 1120 for a USTD in FIG. 11, in order to generate the design of the VTD in Custom Device Manufacturing and Fitting 230 in FIG. 2 or USTD in Custom Device Manufacturing and Fitting 1130 in FIG. 11. Within embodiments of the invention a design selection may be additionally based upon a patient and/or surgeon profile in combination with historic patient or surgeon data in addition to the data derived from the patient's measurements, biometric data etc. to provide enhanced design. For example, in some embodiments, a database may be interrogated to identify prior cases or profiles and their outcomes to assist in the optimization of a design for a current patient or surgeon case. Thus, embodiments of the invention provide for the AI Engine to learn from historical cases with their successes and challenges of variables dealt with in the past. In some embodiments, this may be provided by a case-based expert system (CBES) will provide the AI Engine with data. This CBES allows for the AI Engine to learn from past cases, while focusing on new variables which have not been dealt with in the past. Accordingly, as the VTDs and/or USTDs are established the design/analytics cycle together with biometric acquisition, QoL acquisition etc. will be repeated over hundreds, then thousands, and ultimately hundreds of thousands of cases and the intelligence incorporated into the CBES will enable the AI Engine to increasingly be specific and accurate with features, geometries etc. it designs into these VTDs and/or USTDs. Further, extending the AI Engine's access to other databases will allow long-term successes or challenges of VTDs and/or USTDs to be captured through other registry systems to track patients and their medical data.

The CBES allows correlations between patient profile information and design features and outcome to be identified such that over through the monitoring of multiple patients, multiple product designs, and multiple product design variants over time patterns may be detected that permit a new design to be optimized using historic intelligence from prior patient data of patients that had similar characteristics etc. and achieved desired, optimal, or non-optimal outcome.

Within FIGS. 2 and 11 respectively the AI Engine is depicted receiving data from Assessment and Performance Goal processes within a preceding stage, e.g. Analysis and Modelling 220 in FIG. 2 for a VTD or Analysis and Modelling 1120 for a USTD in FIG. 11, and providing data to a Manufacture process, e.g. Manufacture 232 in Custom Device Manufacturing and Fitting 230 in FIG. 2 or Manufacture 1132 in Custom Device Manufacturing and Fitting 1130 in FIG. 11. However, in other embodiments of the invention an additional stage may be introduced wherein a clinician, physician, or surgeon (hereinafter referred to as an expert) may review the design and provide feedback prior to production of the VTD and/or USTD. For example, in some embodiments, a design that incorporates patient or expert profile information and, optionally, historical case information, is presented to the expert for evaluation. The design is presented to the expert in a manner that permits the expert to evaluate the position and function of the device using 3D CAD models, as well as permitting the expert to observe and test performance parameters using computer simulation. The expert may access the system remotely via a software application in execution upon their computer system coupled to one or more remote servers and/or computer systems. The expert can select or recommend design changes to the AI Engine directly or through an interface of a VTD and/or USTD software system implementing embodiments of the invention. The software system together with the CBES and/or AI Engine can accordingly incorporate patient- or expert-specific needs based on the wisdom and experience of the expert and the new design can be submitted and tested, and if desired, re-evaluated prior to selecting a final design prior to release to production.

Accordingly, upon expert review the AI Engine may perform revisions to the design of the VTD and/or USTD. In this case, a new virtual 3D model can be produced, tested, and re-evaluated. In some embodiments, only following approval by the expert or through a collaborative approval, such as the expert and/or a designer and/or manufacturing authority can a design be released for manufacture. In some embodiments of the invention the VTD and/or USTD may be designed in conjunction with either an intended surgical procedure or with a recommendation that a surgical procedure be performed. In other embodiments of the invention the design process and/or a clinical evaluation may determine that an area or areas of the user should be surgically manipulated, e.g. a re-alignment, sectioning, re-profiling, or morphological adjustment should be performed. Optionally, the design of the VTD and/or USTD may require that a portion or portions of the VTD and/or USTD are attached to the user's body through a surgical procedure in order to ensure appropriate placement and/or retention of the VTD and/or USTD.

As depicted in respect of FIGS. 4, 7C, and 9 a USTD, according to embodiments of the invention may include a wired and/or wireless interface allowing the USTD to be coupled to a remote monitoring/data logging server for example via the user's PED/FED and a telecommunications network. However, it would be evident that other embodiments of the invention such as those in FIGS. 5A-% c, 6A-6B, 7A-7B, 8A-8B, 10, 12A-12B, and 13 whilst not described as containing electronics and/or wired and/or wireless interfaces may within other embodiments of the invention support such components and/or circuits allowing the USTD to be coupled to a remote monitoring/data logging server for example via the user's PED/FED and a telecommunications network. Optionally, the wired and/or wireless interface may allow data to be acquired at discrete time points such as a user's visit to a clinician, physician etc. Alternatively, within embodiments of the invention the wired and/or wireless interface may allow an aspect of the USTD to be adjusted and/or activated. For example, a USTD may include a piezoelectric actuator or micro-motor allowing a dimension of the USTD to be adjusted, e.g. reduce a diameter of an opening within a USTD or expand a ring of a USTD for example. Alternatively, the USTD may include a heater, a vibrating element, or other active elements. Alternatively, within other embodiments of the invention the USTD may be directly coupled to a telecommunications network via a wireless interface or in some instances a wired interface.

The telecommunications network may be coupled to a remote central exchange communicates with the remainder of a telecommunication service providers network via network infrastructure and therein via local, regional, and international exchanges (not shown for clarity to remote servers and/or other devices which may be coupled to the telecommunications network. A USTD, may be coupled to the telecommunications network via a wired interface exploiting a protocol selected from the group comprising, but not limited to, DSL, Dial-Up, DOCSIS, Ethernet, G.hn, ISDN, MoCA, PON, and Power line communication (PLC) which may or may not be routed through a router. A USTD, may be coupled according to their particular communications interfaces to the telecommunications network through one or more wireless interfaces selected from the group comprising, but not limited to, IEEE 802.22, IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, and IMT-1000. Optionally, a USTD may support multiple wireless protocols simultaneously, such that for example the USTD may employ GSM services such as telephony and SMS and Wi-Fi/WiMAX data transmission, VOIP and Internet access. Accordingly, a USTD according to an embodiment of the invention may form an association with a PED and/or FED according to standards such as IEEE 802.15 and Bluetooth as well in an ad-hoc manner as well as a wireless router.

The USTD may link through the telecommunications network to one or more services such as those provided by, but not limited to, the USTD manufacturer, an online retailer, a medical portal, a Government electronic health provider/service, and user cloud biometric data storage. The USTD may also access and/or interact with one or more providers, enterprises, service providers, retailers, Government entities, third parties etc. and other users, for example. The USTD may also directly or via the user's PED and/or FED connect to one or more servers which may support/host according to embodiments of the invention multiple services associated with a provider of USTD systems, applications, and platforms (USTDSAPs); a provider of a SOCNET or Social Media (SOME) exploiting USTDSAP features; a provider of a SOCNET and/or SOME not exploiting USTDSAP features; a provider of services to PEDS and/or FEDS; a provider of one or more aspects of wired and/or wireless communications; an enterprise exploiting USTDSAP features; license databases; content databases; image databases; content libraries; user databases; websites; and software applications for download to or access by FEDs and/or PEDs exploiting and/or hosting USTDSAP features; search engine; third party applications and other Internet based services. Accordingly, the USTD may push data to one or more such services and/or servers for access/retrieval in respect of the ongoing monitoring and assessment of the user's USTD, USTDs to multiple users sharing common design elements and/or materials/structure etc., or all USTDs for example. Equally, a user may monitor their USTD performance and post directly personal comments/notes etc.

Within other embodiments of the invention the user's wearable devices provide additional biometric data which may be stored in association with the USTD data allowing for assessment of the USTD in respect of the specific activities, etc. performed by the user.

Within embodiments of the invention a USTD incorporating an electronic circuit may include one or more processors and one or more memories coupled to processor(s). The electronic circuit may be part of an application specific integrated circuit (ASIC) or part of an application specific standard product (ASSP). The electronic circuit may exploit a protocol stack or stacks such as an IEEE 802.11 protocol stack, for example, or alternatively may exploit other protocol stacks such as an Internet Engineering Task Force (IETF) multimedia protocol stack for example. The protocol stack may be implemented in any combination of software, firmware and/or hardware. It would be apparent to one skilled in the art that elements of the electronics circuit device 304 may also be implemented to support one or more alternative and/or additional wireless or wired interfaces in addition to the described IEEE 802.11 interface which may be selected from the group comprising IEEE 802.11 a/b/g Wi-Fi, IEEE 802.16 WiMAX, and IEEE 802.15 Bluetooth, IEEE 802.20, UMTS, GSM 850, GSM 900, GSM 1800, GSM 1900, GPRS, ITU-R 5.138, ITU-R 5.150, ITU-R 5.280, IMT-1000, DSL, Dial-Up, DOCSIS, Ethernet, G.hn, ISDN, MoCA, PON, and Power line communication (PLC).

Accordingly, the USTD may operate as a standalone device with factory installed control routines accessed through an interface on the USTD, not shown for clarity, or through an application in execution upon a PED and/or FED. Subsequently, one or more of these control routines may be modified, amended, deleted etc. whilst other new control routines may be created, acquired, installed etc. Accordingly, it would be evident to one skilled the art that the USTD may accordingly download original software and/or revisions according to its supported interfaces either directly or indirectly via PED and/or FED. Similarly, the USTD may push data to a cloud storage directly or indirectly via a PED and/or FED. Due to the nature of the USTD it is expected that the majority of designs would exploit a low power short range communications protocol such as IEEE 802.15 Bluetooth low power or Near-Field Communication (NFC) for example. Within other embodiments of the invention the USTD may be passive with the electronic circuit providing data based upon the USTD electronics being energized via an NFC power transfer interface for example. In some embodiments of the invention the functions may not be implemented within the original as sold USTD and are only activated through a software/firmware revision and/or upgrade either discretely or in combination with a subscription or subscription upgrade for example.

Within embodiments of the invention in a measurement and characterisation stage of determining the characteristics of the user they may be asked to wear a device which provides additional data relating to the user in addition to that identified supra. For example, the user may be asked to wear a device which provides for monitoring vaginal exercises, e.g. a Kegel exercise device, as well as providing for other parameters including, but not limited to, labial temperature etc. for indications of whether their symptoms change according to initial stages of sexual arousal, during vaginal exercise etc. Optionally, extended monitoring of the user's labial temperature in conjunction with other biometric data, including vaginal pressure, etc. may allow enhanced determination of the user's exhibition of symptoms alignment with other physical and/or physiological characteristics. Optionally, within embodiments of the invention a thermistor may be employed to provide labial temperature, but this may be replaced by another element with an electrical characteristic that is temperature dependent such as resistance, inductance, or capacitance for example.

Optionally, optical sensor elements may be employed for determining, for example, labial and vaginal blood flow using photoplethysmography (PPG) and/or laser Doppler imaging (LDI). Within PPG exploiting a reflective mode as depicted the volume of blood is determined in dependence upon the intensity of the reflected whilst each cardiac cycle appears as a peak within the reflected signal. As blood flow to the skin can be modulated by multiple other physiological systems, PPG can also be used to monitor breathing (respiration), medication effects, hypovolemia, and other circulatory conditions, especially where extended monitoring under a variety of conditions including rest and/or sleep provide enhanced baseline and/or early data. For example, the height of AC component of the PPG is proportional to the pulse pressure, the difference between the systolic and diastolic pressure in the arteries. Additionally, the shape of the PPG waveform differs from subject to subject, and varies with the location, providing additional options such as identification of user through PPG data and automatic adjustment of the ADDEV parameters/control program etc. in response therefrom.

Alternatively, Doppler imaging (LDI) wherein the OSAD is typically an infrared laser source in conjunction with a photodetector rather than a visible LED and photodetector in the instance of PPG. Accordingly, the pulsed laser light interacts with moving blood cells such that a small portion of it is reflected with a frequency shift, detected, and converted into an electrical signal. LDI can provide measurements without requiring physical contact and the signals are typically acquired at depth of 2-3 mm (approx. ⅛") below the skin surface. Optionally, a device for characterization may employ an array of PPG and/or LDI sensors.

Within other embodiments of the invention a characterization and/or assessment device may exploit multiple electrical contacts (ELCOs) onto its surface. An array of ELCOs may be employed as well as a discrete ELCO and/or spatially separated ELCO pair(s). An ELCO may be employed to measure electrical activity and/or provide electrical stimulation to the user's vagina. Accordingly, the device may provide electrostimulation of the vaginal muscles with part of an exercise/training regime and then determine from user flexing the muscle strength/range of motion etc.

Within an alternate embodiment of the invention one or more of the ELCO elements may be replaced with a microphone such as one based upon capacitive thin film or microelectromechanical systems (MEMS) transducer, a piezoelectric transducer, accelerometer, hydrophone, or another type of microphone in order to measure the acoustic output of a contracting muscle. Accordingly, based upon such microphone placement a characterization device may support phonomyography (PMG) of the pubococcygeus muscle and/or other of the pelvic floor muscles. Typically, PMG has a frequency range of interest that is primarily 5-50 Hz.

Within embodiments of the invention in a measurement and characterisation stage of determining the characteristics of the user a device may be employed which can deform to fit into the vagina and recover to fit against the vaginal walls mapping the user's physiology wherein resistance sensors may map the deformation through strain and/or stress. Alternatively, the device may be a balloon of high elasticity material with stress and/or strain sensors which is filled with a fluid expanding the balloon and the deformation mapped from which the user's physiology is derived.

Within the descriptions supra embodiments of the invention have been described with respect to providing simulation and assessment of a user's vagina, vaginal muscles etc. Electrical control and monitoring have been described together with wired and wireless data connectivity of the USTD to the external world. Accordingly, the USTD may be wirelessly connected to a user's PED or FED and access/ post content/data to one or more local and/or remote servers associated with different aspects of the user including, but not limited to, their personal USTD profile, personal health records, other PEDs/FEDs/wearables, physician's office, etc.

Within embodiments of the invention the USTD contains one or more sensors including, but not limited to, accelerometer, thermometer, LDI, PPG, and a microphone. This or these may be employed to determine heart rate, menstrual cycle, amount of exercise, changes in physical activity level during an exercise session. Optionally, additional sensors such as a humidity sensor may be incorporated into the device or additional biometric data may be acquired through an aggregator USTDSAP such as the user's smart phone for example communicating with the USTD and one or more wearable devices. Accordingly, the USTDSAP and/or USTD can establish whether the user is performing activities such as showering when using the USTD or when an event occurs.

In some embodiments of the invention, various detections, determinations, tracking and storage of aspects and parameters, as discussed herein, are executed wholly or partially internally in the USTD; in other embodiments they are executed wholly or partially in a wirelessly connected standard user interface running software as part of this embodiment; in yet another embodiment they are executed whole or partially by software running remotely upon remote servers or "in the cloud" as colloquially known. In other embodiments the user may be prompted through such a wirelessly connected standard user interface to perform one or more specific actions in isolation and/or in combination with a view to improving or mitigating an aspect of the user's physiological and/or sexual wellness.

In some embodiments of the invention, current exercise parameters and the user's performance/progress are sent to a doctor, trainer or therapist in real-time and/or periodically. In some embodiments of the invention the doctor, trainer or therapist may concurrently within a communication link, such as a phone call, in the reverse direction provide human, personalized instruction, communication, status, or feedback to the user as well as seek additional clarification/ information.

The USTD may be provided in a range of physical sizes such that, for example, the length of an inserted actuated member (e.g. for vaginal insertion) may be 50 mm, 65 mm, 75 mm, 100 mm, 125 mm, or 150 mm for example (2", 2.5", 3", 4", 5", or 6") or other values for this dimension and its lateral dimensions may be, for example, 40 mm, 50 mm, 65 mm, 75 mm or 100 m (1.6", 2", 2.5", 3", or 4") or other values for this dimension. Typically, the construction of a USTD such as depicted within embodiments of the invention described in respect of FIGS. 5A, 5B and 6 may employ one or more central scaffolds which provides rigidity to the required portions of the USTD which may be surrounded by a shell and then a casing. Whilst the casing and shell may be transparent or semi-transparent over portions or all of the USTD it is common for the USTD to be opaque. An outer casing may be coloured based upon skin colour tones based upon ethnicity or personal preference, e.g. Caucasian, Negroid, Mongol, light, dark, etc. as well as single colour, binary colour, multiple colour etc. According to the complexity acceptable then the outer casing may be formed from a variety of colours and/or be patterned for a specific design. Typically, such colours will be part of a silicone or other elastomer employed in forming the casing although in other embodiments of the invention the casing may be coloured once formed and a protective fluid proof, non-toxic, non-abrasive coating formed atop these applied colours. Such instances of applied colours may include metallic lacquers, particulate lacquers for "sparkle", etc. Exploitation of silicone coatings for the flexible shaft between a USTD body and a separate antenna allows similar options although pigmenting of a wide variety of plastics employed in cables etc. may also be employed for outer casings formed from other plastics and/or elastomers.

Beneficially, medical grade silicone is clear thereby removing the requirement for any additional coating (e.g. food grade urethane) in conjunction with pigmented silicones. Accordingly, an USTD may with medical grade silicone be clear and formed from an initial sticky soft silicone, e.g. 20 durometers, with a micro-layer (spray coated for example) of high durometer medical grade silicone, for example 70-90 durometer, to create "slippery" surface and avoid silky smooth surface that typically requires use of urethane coating.

Typically, the casing for the USTD will be formed from a non-toxic, hypoallergenic silicone to provide a safe smooth surface although some regions of the USTD may be coated, textured and/or finished with a variation from that of the remainder of the casing in order to enhance or promote retention of the USTD against the user's skin or clothing. Typically, the outer surface of the casing will be formed to provide low friction as well as resistance to lubricants, spermicides, and other chemicals that may or may not be employed by the user.

Typically, within the outer silicone or elastomeric casing is a shell that houses internally, in the embodiments presented, sensors, cables, electronics, etc. Within embodiments of the invention for characterization and/or monitoring rather than a passive USTD other functional elements may be employed for generating physical stimulus, monitoring physical characteristics, measuring the user's anatomy, etc. Within the description of embodiments of the invention and associated figures such elements are not presented for clarity of description, figures etc. However, such elements may or may not be implemented within embodiments of the invention. Accordingly, for example the core and/or shell may be formed from a single piece part or multiple piece parts which are connected via the casing and/or discrete or connected by a central portion with different degrees of rigidity range from solid to a living hinge.

Optionally, the outer surface of the USTD may provide electrical stimulation and/or measurement contacts through metal contacts or conductive silicone pads.

Optionally, a USTD may comprise a single use and/or rechargeable battery or batteries within the shell which may be of a standard form/type or custom to the USTD and/or another product.

Embodiments of the invention with respect to the USTD such as described within the embodiments of the invention supra may employ a "sticky" surface for a predetermined portion of the outer surface for engaging a recipient's body (e.g. being formed from a low durometer silicone for example) so that the surface is designed to "stick" to skin, so it stays in place or has higher resistance to motion. This "sticky" surface may be mirror surface, matt or textured for grip. Examples of materials may be those with durometer ideal Shore A10 or lower, Shore A5 or lower, or Shore A1. In some embodiments of the invention a region or regions of the casing may be formed from a gel such as the Ecoflex™ platinum catalyzed silicones for example certified to ISI 10993-10 for skin irritation/sensitization and having, for example, Shore 00-50 hardness (below the Shore A scale), Shore 00-30 hardness, Shore 00-20 hardness, or Shore 00-10 hardness. In embodiments of the invention the casing around the shell may act like a thin sheet (<<1 mm thick), like a fabric or material, like a sheet (~1 mm), a thick sheet (>1 mm). Optionally, the lower surface of the casing designed for placement against a user's groin/stomach may be sticky and when washed recover this stickiness in its entirety or in different regions or areas.

Optionally, the outer surface which contact the user may be smooth with low friction to human skin, smooth with minimal friction to human skin, smooth with moderate friction to human skin, smooth with high friction to human skin in its entirety or in different regions or areas. Alternatively, the surface may be smooth, textured, and/or rough and have low friction, negligible friction, moderate friction, and/or high friction in its entirety or in different regions or areas. Optionally, the surface may be textured with low friction to human skin, textured with minimal friction to human skin, textured with moderate friction to human skin, or textured with high friction to human skin in its entirety or in different regions. Optionally, the surface of the casing in its entirety or in different regions or areas may be used in conjunction with disposable sheets that provide adhesion and/or friction in predetermined levels.

Within embodiments of the invention the casing, for example formed from silicone, is the only material surrounding the casing and the surface profile is derived from applying the casing to the contoured surface of the shell. In other embodiments of the invention the surface profile is derived from multiple applications of a single material forming the casing. In other embodiments of the invention an additional material or materials are disposed between the shell and the casing. This, may for example, be a preform formed from the same material as the casing such that the casing is applied as a single or multiple dip coating for example, a preform formed from another silicone of different characteristics to the casing, a preform formed from a plastic, a preform formed from a low density foam, from a medium density foam, or a high density foam. Alternatively, a combination of materials may be employed such as two or more plastics, two or more foams, a foam and a plastic, a foam and a silicone, a form and metal. The materials may be layered, inserted, embedded, etc. without departing from the scope of the invention. However, a characteristic of these materials is the transmission of vibratory motion arising from the active elements within the USTD according to embodiments of the invention. Within passive embodiments this characteristic of material selection is removed.

Within the embodiments of the invention with active elements these are mounted to predetermined portions of the shell which is surrounded by the casing. Other embodiments may exploit a passive inserted portion mimicking a dildo function rather than a vibrator. As noted above the USTD according to embodiments of the invention may, in addition, to a silicone outer comprise one or more materials to provide mechanical structures such as ridges, shell, scaffold, etc. whilst the casing is smooth.

Optionally, the core and shell of the USTD are formed through either one or more additive manufacturing (AM) steps and non-additive manufacturing (NAM) steps. For example, a core may be formed from a metallic powder and binder, sintered wherein the casing is formed by 3D printing of the appropriate polymer and then the casing added by spraying and/or dip coating. Alternatively, the core is formed by convention NAM processes to which a multi-part AM formed casing is attached together with electronics etc., sensors masked and the assembly silicone coated for the casing.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method of providing a vaginal therapeutic device (VTD) for a user comprising the steps of:
   deriving one or more user specific results by performing a characterization process upon the user to obtain at least one measurement of a plurality of measurements of the user;
   generating an anatomical model by performing a modelling process which applies the one or more user specific results of the characterization process to the anatomical model;
   designing the VTD by performing at least one of: computational modelling, finite element analysis, and three-dimensional modelling upon the anatomical model, wherein the VTD comprises at least one structure of a plurality of structures, and each structure of the VTD has a defined geometry and a defined material composition; wherein
   the VTD further comprises:
      a body portion formed from a first predetermined material having a first Young's modulus, wherein the body portion has a first predetermined geometry; and
      a second portion formed from a second predetermined material having a second Young's modulus having one or more sections disposed within the body portion, wherein each section of the one or more sections has a second predetermined geometry; wherein
   the first predetermined geometry, the second predetermined geometry, the first Young's modulus, and the second Young's modulus are calculated in dependence upon the performing of the modeling process and the designing of the VTD; and
   the VTD is one of a ring shaped pessary, a disk shaped pessary, and a space-filling pessary; and
   fabricating the at least one structure of the plurality of structures of the VTD by performing at least one processing step of a plurality of processing steps; wherein
   the at least one processing step comprises an additive manufacturing step of creating a physical version of the at least one structure of the plurality of structures of the VTD; wherein
   performing the modelling process comprises:
      modifying the anatomical model in dependence upon the one or more user specific results derived by performing the characterization process upon the user to obtain the at least one measurement of the plurality of measurements; wherein
   the anatomical model is a model of a vagina, support tissues surrounding the vagina and pelvic organs surrounding the vagina.

2. The method according to claim 1, wherein:
the at least one measurement of the plurality of measurements comprises at least one of:
   a structural measurement by at least one of a manual measurement process, an imaging process and a mechanical process;
   a force or strain measurement by a measurement process comprising at least one of a pressure variation process, a volume determination process and a deformation process to a vagina of the user;
   a quality of life measurement relating to at least one of a symptom of the user and an aspect of a lifestyle of the user;
   at least one of a force measurement and strain measurement taken using an intravaginal sensor device;
   one or more measurements through tactile interaction with the vagina of the user;
   one or more vaginal distention measurements established by at least one of manometry and molding; and
   one or more vaginal measurements of the vagina of the user established via elastography performed at least one of intravaginally and transperineally.

3. The method according to claim 1, wherein:
the one or more user specific results of the characterization process comprises at least one of:
   a characteristic of the user selected from the group comprising bone structure, soft tissue structure, soft tissue strains, vaginal geometry, a statically acquired vaginal measurement, and a dynamically acquired vaginal measurement; and
   a performance goal for the VTD selected from the group comprising a static performance objective of the VTD for the user, a dynamic performance objective of the VTD for the user, an antimicrobial requirement for the VTD, a contraception requirement of the user, and a drug delivery requirement of the VTD.

4. The method according to claim 1, wherein:
designing the VTD comprises defining at least one of:
   a geometry and material of a scaffold structure;
   a geometry and material of a shell structure;
   a geometry and material of a casing structure;
   location and function of an active element;
   location and function of an electronic circuit;
   location of a wireless or wired interface;
   a geometry and location of any lock-release structure; and
   a requirement for any special coating.

5. The method according to claim 1, wherein
the characterization process employs one of a first device or a second device wherein:
the first device comprises:
   a first predetermined portion for insertion into a vagina of the user;
   a second predetermined portion electrically coupled to the first predetermined portion; and
   at least one sensor of a plurality of sensors, wherein the at least one sensor of the plurality of sensors is selected from the group comprising a photoplethysmography sensor, a laser Doppler imaging sensor, a phonomyography sensor, a pressure sensor, a force sensor, a pH sensor, a flow-rate sensor and a temperature sensor; and
the second device comprises:
   a body formed from a highly elastic and deformable material;
   a plurality of sensors disposed upon the surface of the body, each sensor to measure local deformation of the body; and
   a plurality of contacts electrically connected to each sensor allowing local deformation measurements to be taken.

6. The method according to claim 5, wherein:
at least one of:
   the first device or second device when inserted into the vagina of the user allows an internal physiology of the user's vagina to be defined from processing a series of resultant local deformation measurements established in dependence upon data generated by a subset of the plurality of sensors;
   the first device or second device when inserted into the vagina of the user allows at least one of the internal physiology of the user's vagina and deformation of the first device or second device to be defined by one or more ultrasound probes external to a body of the user;
   the body is solid and deforms upon insertion into the vagina of the user before recovering to fit against one or more interior walls of the user's vagina; and
   the body is hollow and deforms when filled with a fluid.

7. The method according to claim 1, wherein:
the VTD comprises:
   a first section comprising:
      the body portion, wherein the body portion comprises a recess on a first side of the body portion and a ring formed around an outermost extent of the recess on said first side of the body portion; and
      the second portion, wherein the second portion comprises a stub portion formed on a second side of the first section distal to the first side, the stub portion having a first predetermined arcuate profile and extending away from the body portion; and
   a second section comprising:
      a knob portion attached to a distal end of the stub portion, the knob portion formed from a third predetermined material having a third Young's modulus; and
      a scaffold formed from a fourth predetermined material having a fourth Young's modulus, wherein a first portion of the scaffold is within the body portion and a second portion of the scaffold is within the stub portion; wherein
   a predetermined portion of the first section and a predetermined portion of the second section form part of a second predetermined arcuate profile.

8. The method according to claim 7, wherein
the second section joins the first section at one end of the first section;
the first section has an upper surface having a first predetermined profile and a lower surface comprising a plurality of ribs which extend along the first section from where the first section joins the second section; and
a distal second end of the first section is closer to the knob portion of the second section than the end of the first section that joins the second section.

9. The method according to claim 1, wherein:
   the second portion comprises a knob portion disposed upon the body portion at a predetermined location extending away from the body portion;
   one or more sensors disposed within the body portion, each sensor at a predetermined location within the body portion and for providing another measurement of the plurality of measurements of the user in dependence upon a predetermined characteristic of at least one of the user and an environment within which the VTD is deployed;
   an electrical circuit disposed within the body portion of the VTD, wherein the electrical circuit is coupled to the one or more sensors and a communications interface; and
   the communications interface operating according to a predetermined protocol and disposed within the knob portion; wherein
the predetermined protocol is one of a wireless communications protocol, a wired communications protocol, an optical communications protocol, and an acoustic based communications protocol.

10. The method according to claim 1, wherein:
   a shape of the body portion is defined by a frustum comprising a predetermined section of a conical body having a predetermined outer profile with a predetermined portion removed such that an inner surface of the body portion has a predetermined inner profile, with an opening at a first end of the body portion and another opening at a second distal end of the body portion;
   the second portion comprises a knob portion disposed at a predetermined position on an external surface of the body portion; and
   a first resilient element of a plurality of resilient elements is disposed within the body portion, each resilient element formed from a third predetermined material having a third Young's modulus and disposed at a predetermined position within the body portion.

11. The method according to claim 10, wherein
each resilient element is arcuate and covers a predetermined angular range of the body portion;
the plurality of resilient elements is two; and
a midpoint of each resilient element of the plurality of resilient elements and the knob portion lies along a common centre line of the body portion.

12. The method according to claim 10, further comprising one or more sensors disposed within the body portion, each sensor at a predetermined location within the body portion and for providing another measurement of the plurality of measurements of the user in dependence upon a predetermined characteristic of at least one of the user and an environment within which the VTD is deployed; wherein
an electrical circuit is disposed within the knob portion of the device, wherein the electrical circuit is coupled to the one or more sensors; and
a communications interface is disposed within the knob portion, wherein the communications interface is electrically coupled to the electrical circuit and operates according to a predetermined protocol; wherein the predetermined protocol is one of a wireless communications protocol, a wired communications protocol, an optical communications protocol, and an acoustic based communications protocol.

13. The method according to claim 1, wherein:
the characterization process further comprises the steps of:
disposing a balloon within a vagina of the user;
coupling the balloon to a device which comprises a plurality of ultrasonic transducers disposed with respect to a fitting to couple ultrasonic signals to and from a predetermined fluid within the balloon;
filling the balloon with the predetermined fluid to a predetermined threshold;
generating the ultrasonic signals with at least one first ultrasonic transducer of the plurality of ultrasonic transducers;
receiving reflected ultrasonic signals with at least one second ultrasonic transducer of the plurality of ultrasonic transducers; and
processing the reflected ultrasonic signals with a processing circuit within the device.

14. The method according to claim 13, wherein:
the device has one of a first configuration and a second configuration;
wherein in the first configuration, the device further comprises:
a first external housing;
a fitting on the external housing having a second predetermined geometry for matching to a first predetermined geometry of a first ring forming part of the balloon;
wherein the plurality of ultrasonic transducers are disposed with respect to the fitting to couple the ultrasonic signals to and from the predetermined fluid within the balloon; and
a processing circuit coupled to the plurality of ultrasonic transducers for generating control signals to the at least one first ultrasonic transducer of the plurality of ultrasonic transducers and processing received signals from the at least one second ultrasonic transducer of the plurality of ultrasonic transducers; and
wherein in the second configuration, the device further comprises:
a second external housing comprising:
a first body portion having a first predetermined external geometry allowing a predetermined portion of the first body portion to be inserted through a second ring forming part of the balloon and comprising the plurality of ultrasonic transducers disposed with respect to the fitting to couple the ultrasonic signals to and from the predetermined fluid within the balloon; and
a second body portion comprising another processing circuit coupled to the at least one first ultrasonic transducer of the plurality of ultrasonic transducers for generating other control signals to the at least one first ultrasonic transducer of the plurality of ultrasonic transducers and processing other received signals from the at least one second ultrasonic transducer of the plurality of ultrasonic transducers.

15. A method of providing a vaginal therapeutic device (VTD) for a user comprising:
deriving one or more user specific results by performing a characterization process upon the user to obtain at least one measurement of a plurality of measurements of the user;
generating an anatomical model comprising a vagina, support tissues surrounding the vagina and pelvic organs surrounding the vagina by performing a modelling process which applies the one or more user specific results of the characterization process to the anatomical model;
designing the VTD by performing at least one of: computational modelling, finite element analysis, and three-dimensional modelling upon the anatomical model, wherein the VTD comprises at least one structure of a plurality of structures, and each structure of the VTD has a defined geometry and a defined material composition; wherein
the VTD further comprises:
a body portion formed from a first predetermined material having a first Young's modulus, wherein the body portion has a first predetermined geometry; and
a second portion formed from a second predetermined material having a second Young's modulus having one or more sections disposed within the body portion, wherein each section of the one or more sections has a second predetermined geometry; wherein
the first predetermined geometry, the second predetermined geometry, the first Young's modulus, and the second Young's modulus are calculated in dependence upon the performing of the modeling process and the designing of the VTD; and
the VTD is one of a ring shaped pessary, a disk shaped pessary, and a space-filling pessary; and
fabricating the at least one structure of a plurality of structures of the VTD by performing at least one processing step of a plurality of processing steps, wherein the at least one processing step comprises
an additive manufacturing step of creating a physical version of the at least one structure of the plurality of structures of the VTD; wherein:
the characterization process is performed with a first device or a second device; wherein
the first device comprises:
a first predetermined portion for insertion into a vagina of the user;
a second predetermined portion electrically coupled to the first predetermined portion; and
at least one sensor of a plurality of sensors wherein the at least one sensor of the plurality of sensors is selected from the group comprising a photoplethysmography sensor, a laser Doppler imaging sensor, a phonomyography sensor, a pressure sensor, a force sensor, a pH sensor, a flow rate sensor and a temperature sensor; and the second device comprises:
  a body formed from a highly elastic and deformable material;
  a plurality of sensors disposed upon the surface of the body, each sensor to measure local deformation of the body; and
  a plurality of contacts electrically connected to each sensor allowing local deformation measurements to be taken.

16. A method of providing a vaginal therapeutic device (VTD) for a user comprising:
  deriving one or more user specific results by performing a characterization process upon the user to obtain at least one measurement of a plurality of measurements of the user;
  generating an anatomical model comprising a vagina, support tissues surrounding the vagina and pelvic organs surrounding the vagina by performing a modelling process which applies the one or more user specific results of the characterization process to the anatomical model;
  designing the VTD by performing at least one of: computational modelling, finite element analysis, and three-dimensional modelling upon the anatomical model, wherein the VTD comprises at least one structure of a plurality of structures and each structure of the VTD has a defined geometry and a defined material composition; and
  fabricating the at least one structure of a plurality of structures and each structure of the VTD by performing at least one processing step of a plurality of processing steps, wherein the at least one processing step comprises
    an additive manufacturing step of creating a physical version of the at least one structure of the plurality of structures of the VTD; wherein
  the characterization process further comprises the steps of:
    disposing a balloon within a vagina of the user;
    coupling the balloon to a measurement device which comprises a plurality of ultrasonic transducers disposed with respect to a fitting to couple ultrasonic signals to a predetermined fluid within the balloon and couple other ultrasonic signals from the predetermined fluid within the balloon;
    filling the balloon with the predetermined fluid to a predetermined threshold;
    generating the ultrasonic signals with at least one first ultrasonic transducer of the plurality of ultrasonic transducers;
    receiving the other ultrasonic signals with at least one second ultrasonic transducer of the plurality of ultrasonic transducers; and
    processing the other ultrasonic signals with a processing circuit within the measurement device.

* * * * *